(12) United States Patent  (10) Patent No.: US 7,212,128 B2
Schenker  (45) Date of Patent: May 1, 2007

(54) MOBILE HEALTH AND LIFE SIGNS DETECTOR

(76) Inventor: Eran Schenker, 14 Israel Galili St., Tel-Aviv (IL) 69377

( * ) Notice: Subject to any disclaimer, the term of this patent is extended or adjusted under 35 U.S.C. 154(b) by 117 days.

(21) Appl. No.: 10/517,274

(22) PCT Filed: Jun. 17, 2004

(86) PCT No.: PCT/IL2004/000537

§ 371 (c)(1), (2), (4) Date: Dec. 9, 2004

(87) PCT Pub. No.: WO2004/110267

PCT Pub. Date: Dec. 23, 2004

(65) Prior Publication Data

US 2005/0225448 A1   Oct. 13, 2005

(30) Foreign Application Priority Data

Jun. 19, 2003   (IL)   ................................. 156556

(51) Int. Cl.
*G08B 23/00*   (2006.01)
(52) U.S. Cl. .................. 340/573.1; 600/300; 600/323
(58) Field of Classification Search ........... 340/870.07, 340/870.11, 870.16, 573.1; 600/300, 301, 600/549, 550, 323; 435/287.7, 287.8; 356/73, 356/416
See application file for complete search history.

(56) References Cited

U.S. PATENT DOCUMENTS

| 3,706,308 | A |  | 12/1972 | John et al. |
| 5,020,528 | A |  | 6/1991 | Myers |
| 5,029,590 | A |  | 7/1991 | Allain et al. |
| 5,853,005 | A |  | 12/1998 | Scanlon |
| 6,118,521 | A | * | 9/2000 | Jung et al. ..................... 356/73 |
| 6,198,394 | B1 |  | 3/2001 | Jacobsen et al. |
| 6,221,012 | B1 |  | 4/2001 | Maschke et al. |
| 6,777,226 | B2 | * | 8/2004 | Jeffrey et al. ............. 435/287.7 |
| 6,830,549 | B2 | * | 12/2004 | Bui et al. .................... 600/549 |
| 6,873,268 | B2 | * | 3/2005 | Lebel et al. ........... 340/870.16 |
| 7,041,063 | B2 | * | 5/2006 | Abreu ........................ 600/549 |
| 2001/0055544 | A1 |  | 12/2001 | Copp |
| 2002/0138009 | A1 |  | 9/2002 | Brockway et al. |

FOREIGN PATENT DOCUMENTS

| EP | 0 846 440 A2 | 6/1998 |
| GB | 2 129 991 A | 5/1984 |
| WO | 01/10295 A1 | 2/2001 |
| WO | 2004/042546 A1 | 5/2004 |

\* cited by examiner

*Primary Examiner*—Van T. Trieu
(74) *Attorney, Agent, or Firm*—The Nath Law Group; Jerald L. Meyer; Derek Richmond

(57) ABSTRACT

A life detector adapted to be used to determine whether an organism or part thereof suits a life condition predefined by a set of ranges, each for a physiological parameter and each characterizing this life condition. The detector comprises a sensor unit adapted to sense at least two of the physiological parameters and to generate signals indicative of their values, a processor for receiving and processing the signals to arrive at these values, the processor further being adapted to disregard any value falling outside the range of the respective parameter and to produce a qualitative diagnosis based on values falling within its range. This diagnosis is indicative of whether the organism or part thereof suits the life condition. The detector further comprises indication means adapted to indicate the diagnosis. The detector may be assembled using a general-purpose programmable communication device, a standard medical sensor and a special cable adapter.

42 Claims, 13 Drawing Sheets

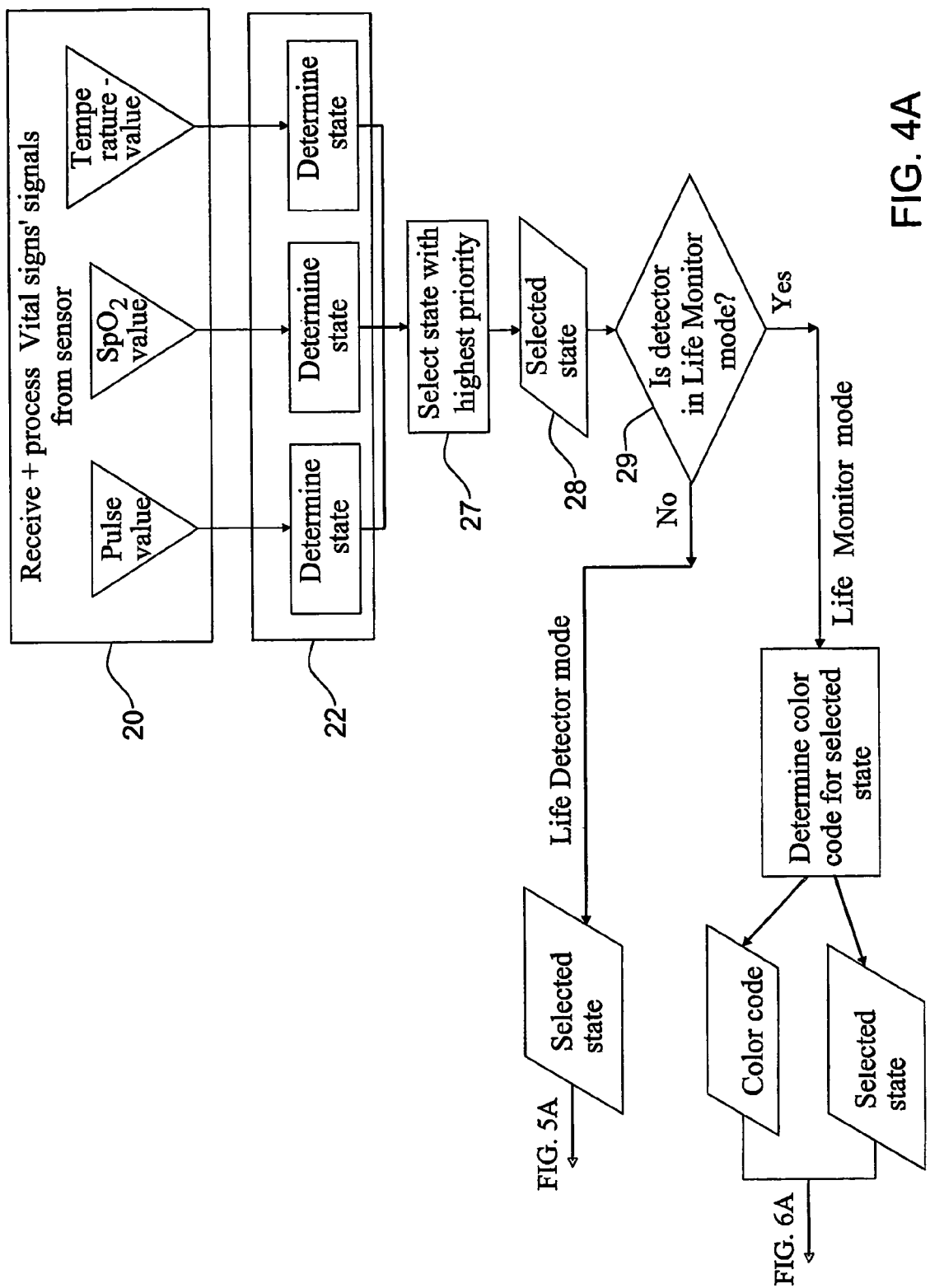

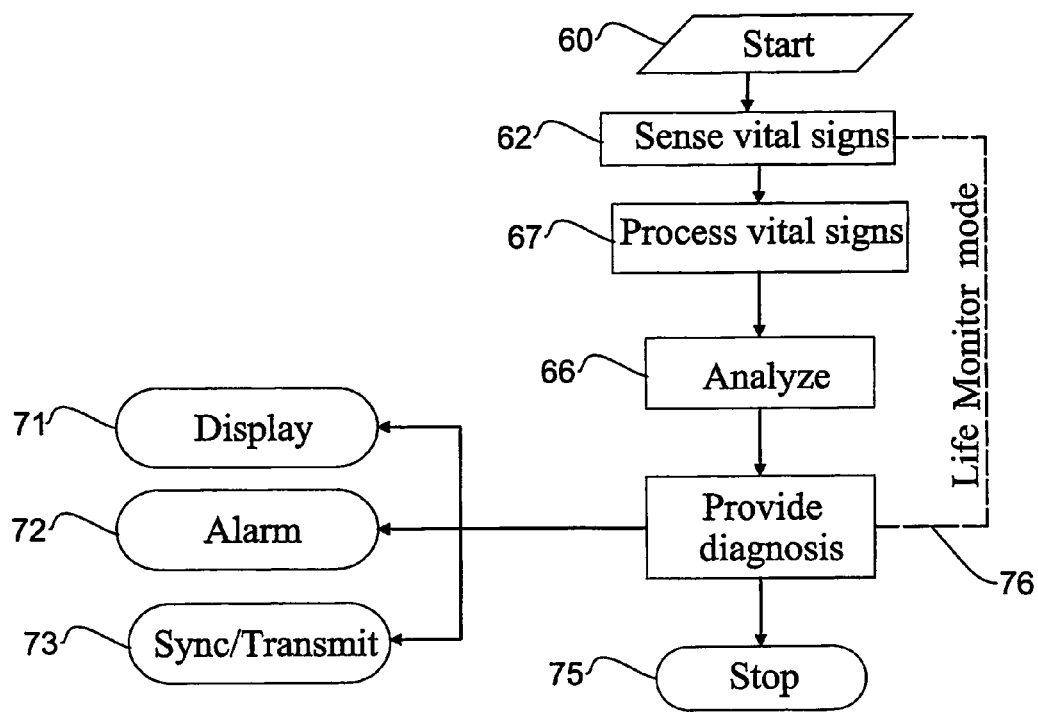
FIG. 7
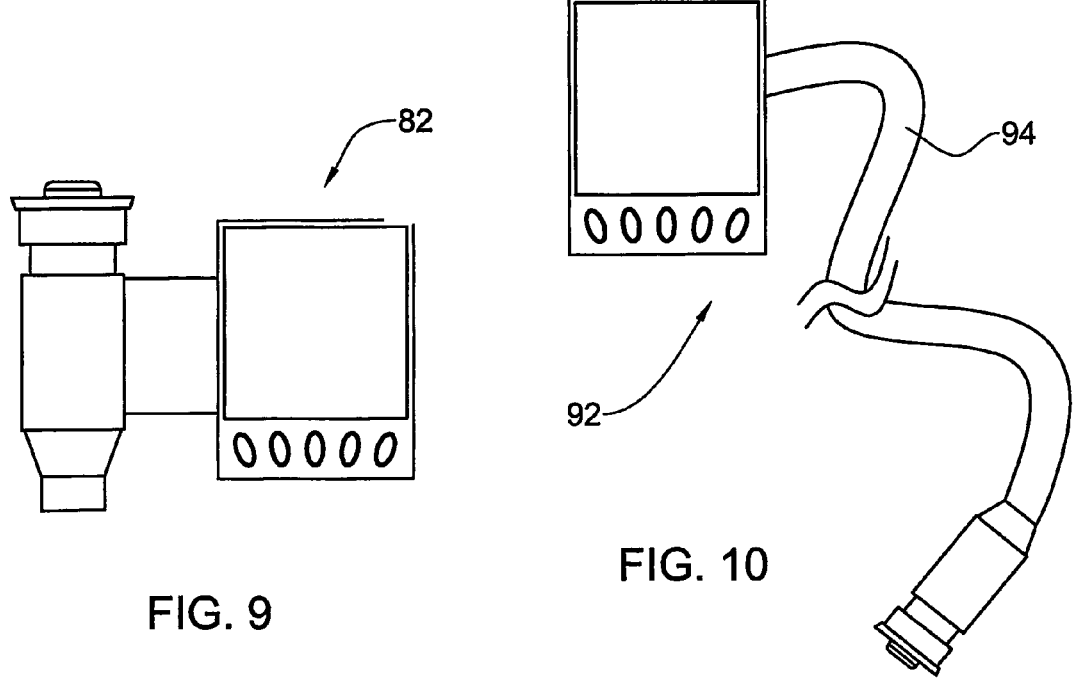
FIG. 9
FIG. 10

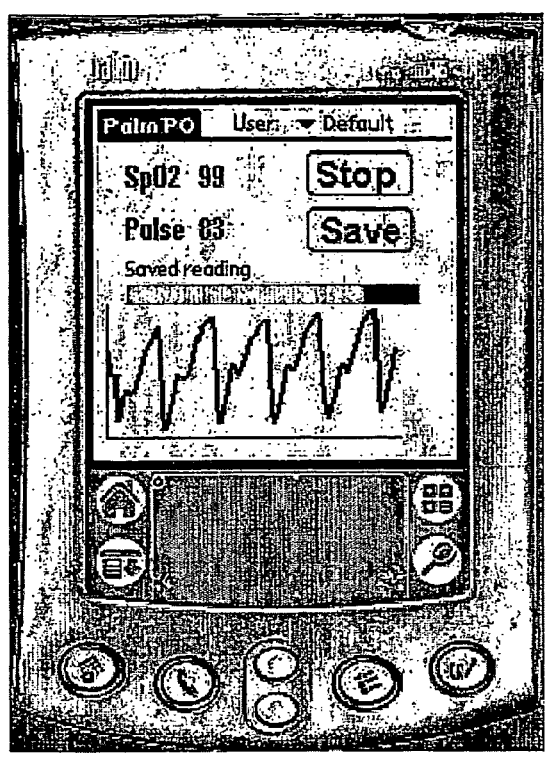
FIG. 8G
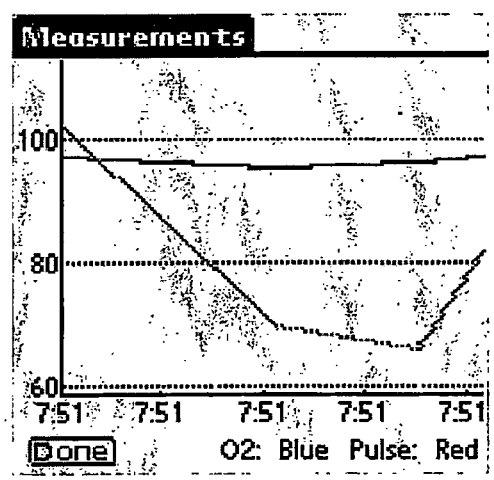
FIG. 8H
FIG. 8I

MOBILE HEALTH AND LIFE SIGNS DETECTOR

FIELD OF THE INVENTION

This invention relates to detectors, and in particular, to those capable of sensing a plurality of vital signs.

BACKGROUND OF THE INVENTION

U.S. Pat. No. 5,020,528 teaches an apparatus for permitting medical personnel to attend to an injured individual situated in a hazardous area from a remote location. One end of the apparatus is adapted to be located at a position adjacent the injured individual and includes sensors for sensing at least one physiological condition of the victim, as well as means for delivering medical aid to him. The other end of the apparatus is adapted to be located at a position remote from the individual and includes means for receiving signals from the sensors to monitor the individual's state of health.

U.S. Pat. No. 5,853,005 discloses a acoustic sensor for monitoring the heartbeat or breathing of a victim. The sensor includes a fluid-filled pad adapted to be held in close contact against a sound or movement source, such as a living human body, and to monitor acoustic signals transferred into the fluid thereby. The signals are monitored aurally and/or compared to predetermined reference patterns, and optional control and stimulation means can be activated in response to the comparison results. The signals can be transmitted to a remote receiver or processed locally.

U.S. Pat. No. 6,198,394 discloses a system for remotely monitoring the status of a plurality of soldiers comprising a soldier unit and a plurality of sensors disposable on each soldier for developing signals used to determine his physiological status. The sensors communicate with the soldier unit, which processes the information to ensure that the sensor data falls within acceptable ranges. The soldier unit also includes a global positioning system and is capable of communicating with remote monitors. By using the sensor data and the global positioning system, leaders and medics can quickly and accurately track and treat casualties in battle. The system enables remote triage/initial diagnosis, thereby assuring that those who are most in need of treatment are attended to first. The system monitors body surface and ambient temperature, heart rate, shivering, motion status and body condition. Additional sensors can be provided to supply information on other physiological parameters that may be desired for more thorough diagnosis.

US 2001/0055544 teaches a portable electromechanical device for locating humans, either living or dead, who are trapped in a structure such as a building that has collapsed or has been badly damaged in an earthquake, mudslide, bombing, or other disaster. This device includes an extendible mechanical detector arm with a handle, and is equipped with a gas inlet device, a miniature video lens and light source, and preferably at least one microphone, all mounted at or near the distal end of the detector arm. The latter components are connected to supporting devices, such as a video display, audio amplifier, and multi-component gas detector, which are either affixed to the handle at the proximal end of the detector arm or carried/worn by a user, allowing him to maneuver the device during a rescue or recovery operation inside a collapsed building or similar environment.

SUMMARY OF THE INVENTION

In accordance with the present invention, there is provided a life detector adapted to be used to determine whether an organism or part thereof suits a life condition predefined by a set of ranges, each for a physiological parameter and each characterizing the life condition. The life detector comprises a sensor unit adapted to sense at least two of the physiological parameters and to generate signals indicative of their values, and a processor for receiving and processing the signals to arrive at these values. The processor is adapted to disregard any value falling outside the range of the respective parameter and to produce a qualitative diagnosis (Vitality Index) based on values falling within its range, the diagnosis being indicative of whether the organism or part thereof suits the life condition. The detector further comprises indication means adapted to indicate the diagnosis.

The range of each parameter includes a predefined set of sub-ranges, each characterizing a particular state within the life condition and each having a predefined priority level with respect to the life condition. The processor is further adapted to determine the particular sub-range in which the value of each parameter falls and the state characterized by said sub-range, and to produce a qualitative diagnosis based only on the state having the highest priority level.

The life detector is preferably adapted to be used by a human operator, the indication means being adapted to indicate the diagnosis to the same operator. When the organism is a human or an animal, the life condition is health condition.

The life detector of the present invention is especially directed to generally diagnosing the health condition of a victim in the immediate aftermath and at the hazard site or extreme environment or disaster event in order to identify quickly and to ascertain the victim's general degree of well being. Examples of particularly applicable scenarios include those in which one or more victims may be trapped, such as under the rubble of a collapsed building or within a severely deformed vehicle, but also include incidents in which victims are scattered over open ground. These situations may be the result of natural disasters such as earthquake or avalanches, terrorist attacks, such as bombings, acts of war on the battlefield, missile strike or in civilian areas, such as following a nuclear, biological, or chemical exposure, as well as automobile or fire accidents.

Whatever the nature of the tragic event, the detector of the present invention enables obtaining an immediate qualitative diagnosis for a victim of the event that may be quickly and easily understood by a non-health professional i.e. one who lacks medical training, particularly the ability to independently assess, without the detector of the present invention, the victim medical condition based on his/her vital signs and physiological or other medical parameter. In this way, the present invention allows for the establishment of a treatment priority for the casualties of the event by ruling out those who will not benefit greatly or at all from immediate treatment, such as the deceased, lifeless or lightly injured, and identifying those that are most in need of treatment and/or evacuation so that they may be attended to first.

The detector of the present invention is adapted to provide a rapid qualitative diagnosis as to whether a victim possesses a predetermined health condition, such as that of "alive" or "abnormal" or "no life detected", even before the victim is rescued, evacuated, or freed, if trapped. Nevertheless a "no life detected" does not mean in all cases "lifeless" or even "deceased". There are cases the detector, from different direct or indirect factors, may not be able to produce a reasonable output, e.g. bad sensor connection, communication error and others.

Preferably, the detector of the present invention is adapted to determine whether the victim possesses a predetermined health condition, which is a positive state of being. e.g. "alive", "normal", "healthy", and other such desired health conditions.

In addition, the present invention may also provide a rapid qualitative diagnosis indicative of the victim's departure from the predetermined health condition. Furthermore, a number of such qualitative diagnoses may be compiled, thereby allowing for a quick general assessment of a disaster situation including the number of casualties and their extent Such information is extremely beneficial in such situations as it enables the establishment of a treatment priority for the causalities, and also permits the determination of the resources, such as manpower and supplies, necessary to treat and save injured survivors. This clearly increases the efficiency of a rescue operation and also maximizes the final number of survivors, as well as the likelihood of their healthy recovery.

The term 'organism', as it appears in the present description and claims, refers to the living body of a person, an animal or microorganism, or part of a living body, on which the detector of the present invention is adapted to be used.

The term 'victim' applies to a person or animal especially in the time immediately following a situation in which the person or animal may have been injured or can be injured in the near future. This particularly includes, but is not limited to, a survivor of an accident or disaster regardless of the survivor's extent of casualty, as well as a fatality of such situations.

The term 'operator', as it appears in the present description and claims, refers to any person or automated apparatus (robot) operating or making use of the device of the present invention to determine a life condition of an organism, as well as to possibly locate, monitor, assess, treat, rescue or otherwise aid a victim.

The term 'life condition', as it appears in the present description and claims, refers to the potential life status of an organism, such as "alive" or "lifeless", or to health condition.

The term 'health condition', as it appears in the present description and claims, refers to a victim's potential health status, such as "abnormal", "healthy", "alive", or "lifeless", which is defined by a plurality of physiological parameters, such as pulse, blood oxygen saturation ($SpO_2$), temperature and others each of which spans a range characterizing the specific state.

The term 'qualitative diagnosis', as it appears in the present description and claims, refers to a general interpretation of an organism's life status or a victim's health status in a manner that may be understood by an operator who is not a biologist or a medical professional. This is accomplished by focusing on one of the main objectives of the invention as the autodiagnosis technique of the detector combined with the Vitality Index analysis.

This technique is called observation accumulation. There are two ways to use the observations in onstage diagnosis: all previously used observations have to be of this type of method and in multi-stage diagnosis: all previously used observations are erased from memory and only newly obtained observations are used to update estimates. This invention makes use of both methods to arrive into conclusions.

The sensor of the detector of the present invention may include a sensor of any known kind so long as it is capable of sensing at least two physiological parameters. Preferably, the sensor is optical and is able to sense at least the pulse and blood oxygen saturation level of the victim, e.g. a reflectance $SpO_2$ pulse oximeter, which senses using beams of both red and infrared light Such a sensor may be provided with a protruding cover to protect its optical mechanism and to prevent external light from entering it and affecting its sensing operation. In addition to the two preferable parameters mentioned above, the sensor is desirably capable of at least sensing the victim's body temperature. Such temperature sensing may also be performed by an optical sensor.

The sensor of the detector according to the present invention may include several separated or combined components, all of which are directed to sense a victim's vital signs and transfer the signals generated from their sensing to the processor. For example, in addition to an optical sensor for sensing pulse and blood oxygen saturation level, the detector may comprise an ECG, EEG or may alternatively have means for connecting thereto. Also, a plurality of sensors may be combined to form a sensor unit directed to sensing, perhaps in a variety of ways and using different technologies, the victim's physiological parameters.

For an optical sensor of the detector according to the present invention, it is preferable that direct or near direct contact be made between part of the body of the victim and the sensor in order to sense. Therefore, the sensor of the detector according to the present invention may comprise a mechanism, such as a spring-based sensing element, to indicate when the sensor has actually contacted the victim's body surface. Conversely, the pressure regulator may also serve to prevent the sensor from being pressed too strongly against the victim's body surface. This is beneficial, for example, for sensing at certain locations on the human body, where over-pressing can result in a considerable change or even halt in the local flow of blood, fluids and others maters, thereby possibly affecting the accuracy of the sensed values.

Certain sensors, which may be incorporated in the detector of the present invention, do not require direct contact with the body of the victim. Such sensors may be able to sense at some distance from the body or through the victim's clothing. Temperature sensors are known, for example, which are capable of measuring temperature of rather distant objects and may also be used in the detector of the present invention.

If the detector according to the present invention is only needed to provide a rough qualitative diagnosis of the health condition, it is not imperative that the sensor be highly sensitive or extremely accurate, especially if the predetermined health condition (e.g. "alive") is based on many parameters and/or does not require high sensing accuracy to be diagnosed. In such a case, the extent of deviation from the particular state, such as "good health", of the victim may not be accurately assessed, but the question of whether the health condition (e.g. "alive") is achieved will likely be correct. For this reason, the sensor may therefore also be applied to virtually any location on the victim's body, even if the location does not provide optimal readings. This is especially advantageous in disaster situations where access to a specifically desired part of the victim's body may not be possible.

The processor of the detector in accordance with the present invention functions according to a specific algorithm, which directs the processor to ignore any sensed value of a physiological parameter having a value outside the range defined for that specific parameter defined as characterizing the health condition.

The algorithm directs the processor of the detector according to the present invention to process the sensed values of all the physiological parameters, including physical, chemical, and biochemical parameters, of the victim so as to arrive at an interpretation or qualitative diagnosis of the victim health or medical condition. This algorithm may direct the processor to give various kinds of qualitative diagnoses, such as those indicating whether the victim is living or dead, and/or the extent of casualty such as lightly, medium seriously or critically wounded. The detector thereby provides an immediate on-site interpretation of the victim's medical condition and is therefore especially suited for use by the layman i.e. those without a medical background, but may clearly also be used by medical professionals.

The indication means of the life detector according to the present invention may provide the diagnosis in a variety of ways, including visually and/or aurally such as by a light emitting diode that flashes or an alarm that sounds when the predefined life/health condition is detected. Preferably, the indication means is in the form of a display device having computing abilities, such as a communication device like cellular phone, a Sony™ Clie™, a Cassiopeia™ IPAC™ and other such Windows™ CE devices, a "Palm OS"™ Palm Pilot™ and other such Palm devices, as well as any other pocket PC "palm-sized" processing head-on display devices or others. Such devices advantageously contribute to the detector of the present invention as they combine the indication means and processor in one unit, are lightweight, portable, and require little operating power. Such devices are also commercially available, typically possess high processing speeds, and are capable of displaying the extent of deviation from a particular state and the health condition of a victim, as well as other relevant information in the form of sound, color, and graphics. Such a device also allows the storage of information locally as well as on various magnetic media, such as diskettes, disks, memory devices. The indication means may also have the ability to receive the sensed values of the victim's physiological parameters and to display them for use by a health professional who may require such data to give a more detailed diagnosis and prognosis, if the situation permits.

The sensor, processor, and indicating means of the detector according to the present invention may be in the form of separate communicating units, or any two or all three may be embodied in one component. These components may have the ability to electromagnetically send and receive information between one another, as well as to and from a remote location by all means of communications like radio frequency (RF) and Blue Tooth™ infrared transmission, for example. The latter possibility may be beneficial as the sensed information and/or diagnosis may be sent to a distant location where a person, such as a health professional, may verify or oversee the diagnoses of many victims. In this way, the entire rescue operation of a multitude of victims may be supervised from a remote location since the diagnoses may be sensed and transmitted to thereto by a plurality of detectors simultaneously.

The detector in accordance with the present invention is preferably portable and may have a variety of possible designs, each of which may be suited to its application in particular scenarios. For example, the detector may be a small hand-held unit adapted to be clutched by the operator and pressed against a victim to obtain his diagnosis. The hand-held unit may have means for ergonomic use by the operator, such as by including a glove-shaped member for carrying the unit. Alternatively, the detector may be in the form of a rigid rod, with the sensor mounted at one end and the display being mounted on the other end, while the processor may be located anywhere along the rod. The rigid rod may have a telescoping design or have other means for adjusting its length, and may include a handle to enable ergonomic carrying by the operator. The handle may include buttons for activating and operating the detector, which may further include a strap or other means for being supported on the operator's body. The design of a detector rod allows the operator to hold the detector by the handle and sense victims that he is unable or unwilling to approach by bringing the sensor into contact with their bodies via the rod. Such a rod is especially advantageous in situations, such as the collapse of a building, where only limited access, such as a small crevice, is available by which to reach the victim's body. Similarly, the distance provided by the design of the detector as a rod may serve to separate the operator from the victim, who may be infected by a pathogen or covered by with a hazardous agent In addition, in place of a rod, the display and the sensor of the detector may be separated by a long cable, thereby enabling the sensor to be lowered into a collapsed mine where victims may be trapped, for example. In all possible designs, including those described above, the detector may be preformed according to the specific design with the sensor, processor, and indication means being integrally attached, or alternatively, these components may be adapted to be removably joined to each other or to a certain frame, such as the rod, as desired.

The detector in accordance with the present invention is preferably also equipped to aid the operator in locating victims. To enable the detector to achieve this end, especially in situations where the operator's direct access to the victim is difficult or impossible, it may further include visual aids such as a color video camera, a thermal camera, a powerful light source, and/or other known devices for enabling the operator to locate victims at the site of a disaster. For example, the thermal camera may be specifically adapted to identify areas having temperatures between 32 and 40° C., as these may be indicative of the presence of a living victim. The images from both the video and thermal cameras may be overlapped and displayed by the detector's indication means to conserve space while at the same time enabling the operator to search in a more informative and efficient manner. The cameras may also include optical enhancement means e.g. telescopic attachments to view distant objects and microscopic attachments to view and analyze microorganisms such as those resulting from biological weapon attacks or others. Alternatively, the detector may include additional cameras capable of performing the latter as well as additional desired operations. Such devices may be attached to the end of the detector when in the form of a rod or a cable and are preferably small so that they may be easily inserted into small crevices and enclosures. The camera, light source, or other visual aids may have the ability to change their orientation with respect to the detector at the operator's direction. This is particularly useful when these components are attached to the end of the detector rod or detector cable and inserted into dark, cavernous places to thereby enable the operator to remotely search for victims in a various directions with relative ease.

Possible additional components which may be included in the detector of the present invention to facilitate the operator in locating victims include audio aids such as a microphone to detect noises emanating from a victim such as breathing, knocking, grunting and calls for help, particularly when the victim is situated in a location not easily accessible by the operator directly. The detector may also include speakers or similar devices for producing sounds or instructions that may help alert the victim to the searching operator and encourage the victim to call for the operator, if possible. The microphone and speakers may also serve as a means for communication between the victim and operator once the victim has been located. This audio system may then be used to transfer words or encouragement, instructions, diagnostic questions in order to arrive at an anamnesis for the victim and other such kinds of conversation between the victim and operator. Other possible audio aids include a recording device for recording sounds, such as voices for subsequent identification, and a sound detector to detect sounds or vibrations which may not be audible or discernable to the operator, which may be analyzed by the processor e.g. to identify patterns potentially indicative of trapped victims. The detector may additionally have means for connecting headphones thereto.

Other components which may be included in the detector of the present invention to aid the operator in locating victims include a gas detector especially adapted to identify areas having gas concentrations indicative of a living victim presence. Such gas detector may detect $CO_2$ concentration levels, for example, which are known to be significantly higher near the face of a breathing victim in comparison to the atmosphere.

In addition to its capability of specifically sensing at one instant to arrive at an immediate diagnosis, the sensor of the detector in accordance with the present invention may further be used to monitor a located victim for any change in the health condition or in the extent of deviation from a particular state by continuously sensing and diagnosing. This may be particularly advantageous in situations where the health condition intended to be determined is one of "normal" or "healthy" and where it is desirable to be able to monitor any deviation therefrom to an "abnormal" or "unhealthy" condition and to ascertain the extent of such a deviation. To achieve this purpose, the sensor unit may have means for attaching to the body of a victim and detaching from the detector. For example, the sensor unit may be in form of a cartridge, which comprises a plurality of sensors for monitoring many physiological parameters. The operator may subsequently leave the vicinity of the victim, taking along at least the indication means capable of wirelessly communicating with the sensor unit to provide constant diagnoses of the victim's condition. This may be useful, for example, in a situation where the operator cannot immediately reach the victim and needs to call for reinforcements or retrieve additional supplies or equipment, but deems it desirable to monitor the condition of the victim while he is away. Other components, such as the visual and audio aids, may also aid in monitoring the condition of a victim in a similar manner as that described above by being detached and left with the victim to transmit information regarding his state to the operator's indication means.

The detector in accordance with the present invention may further be adapted to provide a victim with medical, nutritional, or other forms of treatment that may be critically needed such as in cases where a victim is located and requires immediate medical attention to survive. Such forms of treatment may include medical life support, provision of medication, prevention treatment, fluid and nutritional supplements, and inhalation. The detector of the present invention may be applied in crash injuries, where treatment must be commenced on-site with pre-hospital intravenous therapy, which is vital in preventing renal failure. Such treatment may be provided by the detector of the present invention, as well as other forms of treatment particularly applicable to crash incidents including oxygen therapy, fluid therapy, analgesia, and monitoring of the victim's pulse and temperature. The detector may also include means for treating an abnormal health condition of a victim likely to result from disasters and accidents such as hypothermia, hypoxia, tachycardia, brachycardia, and other respiratory and cardiac conditions. Another applicable scenario includes a victim that may be in desperate need of oxygen but is trapped within a severely crushed and damaged train car following a serious accident and cannot be immediately evacuated but may be accessed via a small crevice in the car wall. In these and similar situations, the detector may include means for treating the victim on-site. Such means may include, for example, an air line channel to enable the delivery of air or other gases and gas mixtures e.g. pure oxygen, which may be used to supply oxygen to a victim, for example, or to ventilate a space filled with smoke or other such airborne debris. The detector may also include means for heating or cooling the air supplied by the air line channel, which may be needed to heat or cool a victim and/or the enclosed space in which he may be trapped. The detector may comprise an infusion line channel enabling the delivery of substances such as medication or fluids such as glucose to the victim whether orally, by a syringe and needle coupled to the channel, or otherwise. The detector may be equipped with a medical channel to deliver various forms of medical treatment to the victim, such as pills, syrups, ointments, and other forms of medication to appropriate parts of the victim's body including medications specifically directed to disaster situations, such as atropine in cases of biological warfare attacks. The detector may comprise other medical treatment mechanisms such as a defibrillator to provide an electric shock to a victim suffering from a fibrillating heart or cardiac arrest, or ventilator in case of respiratory difficulties. The use of such mechanism and medications may be initially prescribed by the processor, which may include an algorithm to provide the operator with a prognosis based on the sensed information of the victim. This may be extremely beneficial for cases in which the victim requires urgent medical care and medical professionals are unavailable or delayed. The prognosis provided by the processor may be displayed by the indication means and/or automatically administered to the victim by the detector. Additional mechanisms may be included with the detector of the present invention to provide the kinds of treatment known and likely to be useful in disaster situations such as means for relieving pain, aiding breathing, widening of bronchial tubes, suppressing cough, treatment for crush syndrome and so on. Also, means for supporting or strengthening the immune system may be especially applicable, such as provision of antibiotics or vaccines for tetanus, anthrax, other pathogens and hazardous agents. It may also be useful to include with the detector means for treating common health disorders that are not the result of the disaster but may be exacerbated thereby, such as diabetes or asthma For trapped victims and particularly for victims of chemical, biological, and nuclear accidents or attacks in which immediate rescue is not possible and risks of spreading contamination exist, it may be especially useful for the detector to comprise means for removing contaminants, as well as for taking medical samples from the victims to be transferred to a location where they may be tested and analyzed. For this purpose, the detector may comprise a suction channel to remove by force of suction bodily fluids and other undesirable substances, as well as small fragments of debris near or covering a trapped victim. In most cases, the above-described and other treatment means are intended to simply prevent the victim's situation from deteriorating until a medical professional becomes available and/or evacuation of the victim becomes possible.

All of the above mechanisms and components are preferably arranged and/or equipped in a manner to suitably protect them from damage. For example, the indication means of the detector in accordance with the present invention is preferably provided with a waterproof plastic cover, and the sensor, if optical, may include and automatically retractable shutter to protect its lenses.

The detector according to the present invention is preferably battery operated and includes means for enabling the detector to be recharged. Additionally, the detector may operate by direct connection to an electrical power source.

The detector of the present invention may include additional mechanisms and/or means for attaching thereto known to be useful or applicable to such search, rescue, and recovery situations as described above. For example, the detector may include a breaching mechanism capable of drilling through a wall or collapsed building debris in order to create a means of access to trapped victims.

The detector of the present invention may also be used in a wide number of possible scenarios and applications. For example, suicide terrorists carrying explosives may drop to the ground after being shot by police officers, but since the officers are often unsure as to whether the terrorist has been killed; they refrain from approaching the body as he may be waiting for their approach to detonate the explosives. In such cases, it is known to send a robot to prod the terrorist's body to see whether he is still alive and to unclothe him to assess whether and to what extent he is armed with explosives. The detector of the present invention may offer an alternative method for handling such situations if carried by the robot and used to determine whether the terrorist is alive or not. In such a way, the incident may be brought to an end in a simple, clean, and less dramatic manner.

The detector of the present invention is especially suitable to be used in mass disasters, where the number of casualties may be in the hundreds or more. In such a situation, many operators, each equipped with the detector of the present invention, may scour the scene of the disaster locating victims and assessing their general state of health. This information may be transmitted wirelessly, for example, to a central command center from which the disaster may be supervised and the treatment, rescue, and evacuation effort may be coordinated using GPS (Global Positioning System) capabilities. The information may be in the form of a general indication of the state of the disaster's victims such as by providing the number of alive and dead, as well as the number of lightly, moderately, seriously, and critically wounded victims. Also, the information may be more detailed, such as by including actual vital sign readings for each victim, enabling a health professional to better evaluate the condition of each victim and possibly communicate with the operator who found the victim using the detector of the present invention with instructions as to how to treat the victim.

Another component which may be included in the detector of the present invention to aid the operator in identification of the victim is any identification (ID) reader like barcode ID reader, able to receive the ID of the victim from his personal electronic or other ID card including his medical personal record. Moreover if the victim has internal or external vital sign or other medical monitor connected to the user it may have a way to communicate and receive more medical data prospectively on time scale as well as for other parameters.

The detector of the present invention may be adapted to read biochips, which are known to be implanted under the skin of animals, such as pets, and which may also be implanted in humans. In this way, the detector of the present invention may be able to access and display information stored by these biochips, including medical history, blood type, allergies and vaccinations, for example, of the person or animal carrying the biochip, as well as their personal details, such as name and address.

Furthermore, the detector according to the present invention may be used to train, prepare and practice operators before its actual use thereby in disaster and accident situations or others. Presently, search and rescue personnel practice either with a non-living victim dummy shaped like a human victim or with living and healthy human volunteers which acts as part of a "Human Patient Simulation" (HPS). In these cases, however, the training personnel are aware before the training exercise begins that the "victims" they will locate and diagnose under a simulated collapsed structure, for example, will either be healthy, in the case of volunteers, or "lifeless" i.e. devoid of life signs, in the case of dummies.

To overcome the above and enable training personnel to encounter a wider range of medical emergencies scenarios, without prior knowledge of their diagnoses, the detector of the present invention may be adapted to operate in a "training mode", which the inventor of the present invention has named "TriageSim", and in which the detector provides a random or preprogrammed medical vital signs parameters correlated to a specific diagnosis from a set of programmed sets of rules, regardless of the use or results of the sensor.

The TriageSim is able to operate as a "wrist watch" with a display for the vital signs and other medical information like medical history, blood type, allergies and vaccinations, or as a barcode bracelet with a hand-held "TriageSim" display device having computing abilities. One of the unique functions of the TriageSim is the "dynamic training mode". The CPU and the TriageSim software in it are able to produce a "real time" dynamic ongoing variability and trend of medical parameters. Like in any living organism, even the-so called "constant" parameter in steady state like heart rate has a cycle or a set of variable parameters in any given time. Moreover change in the medical parameters may take place slowly in time and the TriageSim is able to simulate this dynamic trend and display it on the wrist screen or other place.

The TriageSim wrist or the hand-held device has input buttons for the operators, the trainee, as well as for the instructor to communicate with it. Like answering medical questions that the TriageSim display regarding the next step from a preset of a "medical action list" the trainee would have done in the event of a real case based on the set of variable parameters displayed. Or the TriageSim wrist or the handheld device may display a differential diagnosis from prepared chosen options as well what treatment have been given or should be given in real life, based on the parameters displayed for the "victim". The TriageSim is able to record and calculate the time it takes the trainee to conclude each phase of diagnosis and treatment with a simple input of the trainee by pressing on the "arrived" or "conclude" or "next" button. This dynamic communication enables the device to act in response to the input and to produce improvement trend if the trainee have done the right medical diagnosis and treatment, as well as display a deterioration trend if the trainee have got a wrong medical diagnosis and have not given the proper treatment.

The device has the ability to modify the set of variable parameters in a preprogrammed timeline or by the response or the time it takes a trainee to arrive to a diagnosis and treatment in each case, after the trainee has passed given phase of the simulation.

The TriageSim can work as one in a network of TriageSim's with interconnection as well working station on a handheld device or PC. This able the educator instructor of the drill of the TriageSim monitor what a trainee act and do in each minute from his PC main station or his field handheld computer, what he have done, in what order and how long it took him for one "victim" as well as for a set of "victims" which may simulate multi casualty event With the TriageSim system the educator instructor can monitor the order of the patients that where treated, how long in each one the trainee have stayed, how many times and when in what order he arrived again for reevaluation of the dynamic state and to continue to treat the ones who need it.

All the data can be transmitted or transferred online or in the end of the drill and be evaluated to produce a more accurate grade to the trainee, with remarks exactly where he has done right and where wrong and in what way. Comparing to himself in previous simulating as well to others.

In this way, the skills and readiness of training personnel (i.e. potential operators of the detector) may be enhanced in preparation for use of the detector, such as in a real disaster situation.

The life detector of the present invention may be used to detect the presence of living microorganisms, such as bacteria, viruses, etc. This may be particularly useful in screening areas for the existence of pathogenic or harmful organisms, such as biological warfare agents, in an effort to determine whether they are safe to enter. Also, the detector may be used to detect whether a particular space is sufficiently sterile or at least "clean", such as an operating room or a kitchen, by detecting if the space includes living microorganisms and may therefore not be adequately safe for use. To this end, the detector can be equipped with appropriate biochemical, chemical, and/or physical sensors directed and adapted to detect unique physiological parameters of such organisms.

The life detector of the present invention may be in the form of a handy or large scanning detector, similar to handy or corridor metal detecting devices as typically utilized in airports and may in fact be incorporated into such devices. In this way, persons may walk through or beneath such devices and be scanned for the presence of unique life signs or physiological parameters which one may like to detect regarding human and or microorganisms. Especially extremely harmful pathogens, such as Anthrax and Ebola, which may be used in biological warfare or terrorist attacks or others like SARS, HIV, etc. By the unique "fingerprint" of a combination of quantity as well quality of the different characteristic parameter of the subjects looking for. One way to detect those "finger print" characteristic parameter may be remote scanned optically or can aid by a positive or negative air sample device for a more specific advance testing mechanism by having a flow of the substance looking for near the sensor that is in the handy or corridor detecting device.

The life detector in accordance with the present invention may be used to detect whether any organism is alive, including astrobiology (extraterrestrial) organisms. For example, the life detector may be used in missions to other planets to determine whether astrobiology organisms are with signs of life, or at least possess any of the same qualities as living organisms on Earth. In such cases, the ranges defining the state of "life" may be adjusted to suit specifically sought or expected organism, such as microorganisms.

According to another embodiment of the present invention, the life detector has a modular sensor unit comprising a permanent base and a number of changeable sensor or treatment modules detachably attachable to the base. The changeable modules have identical means for attachment so that they are interchangeable among themselves. A dummy module, which is interchangeable with the sensor and treatment modules, may be used.

According to another aspect of the present invention, there is provided a cable adapter for use with a general-purpose programmable device (PD) having indication means, and a standard medical sensor. The cable adapter is capable of interfacing the PD to the medical sensor, after a driver program specifically directed to use with the medical sensor, the cable adapter and the PD is loaded into the PD, so that signals generated by the medical sensor could be processed and suitably presented to an operator by the indication means. Such cable adapter may transforms the PD into a control, indication and communication panel of the above-described life detector.

The interfacing includes maintaining correct input and output voltages and scaling of signal data between the PD and the medical sensor, and providing electric power from said PD to said medical sensor. Preferably, the PD has remote communication capabilities and the driver program is adapted to use them so that data associated with the medical sensor can be transferred to a remote location. Preferably, the driver program is capable to work with a plurality of different medical sensors and/or with a plurality of different PDs.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 4A–4B show flowcharts for qualitative diagnoses in one embodiment of the detector in accordance with the present invention;

FIG. 7 is a flow chart of the diagnostic process in accordance with the present invention;

FIGS. 8A–8I show various data processing functions on the indicator of the detector;

FIG. 9 shows an embodiment of the life detector of the present invention in the form of a hand-held device without shaft and handle;

FIG. 10 shows an embodiment of the life detector in the form of a cable detector;

DETAILED DESCRIPTION OF THE INVENTION

Figure 1:
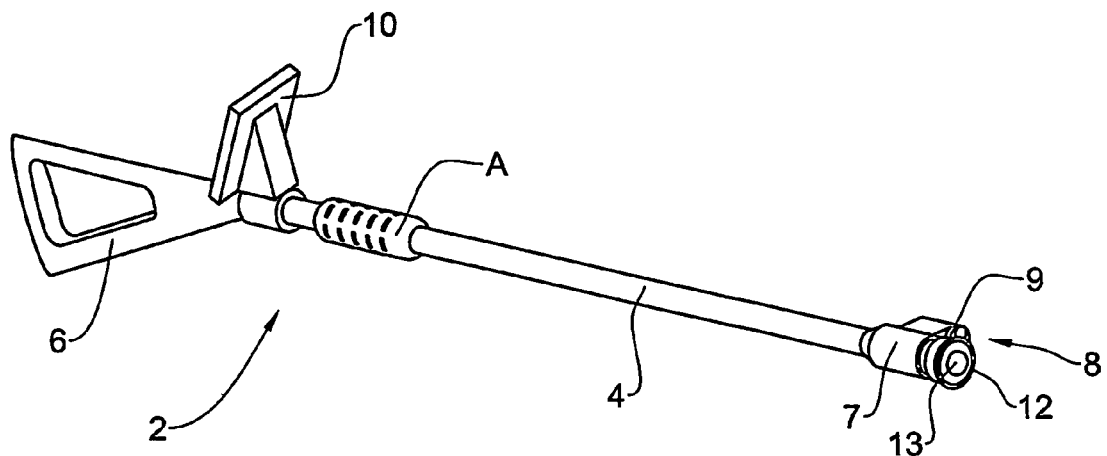
FIG. 1 is a side perspective view of the life detector in accordance with the present invention.
Figure 2:
FIG. 2 is a rear perspective view of the life detector shown in FIG. 1.

FIGS. 1 and 2 show a lightweight, portable rod detector 2 in accordance with the present invention shown from two different perspectives. The detector 2 is adapted to be carried by an operator in order to locate a victim (see below, FIG. 12) and to provide a diagnosis as to whether the victim is alive. The detector 2 is further adapted to provide an extent by which the victim deviates from a stable state of life.

The rod detector 2 comprises a cylindrical rigid shaft 4 with a handle 6 formed at one end of the shaft 4 by which the detector 2 is adapted to be carried by its operator, and a detector head 7 mounted at an opposing end of the detector 2. The head 7 of the rod detector 2 comprises an optical sensor 8 located in and being adapted to be pressed against a body of a victim to enable the sensor 8 to sense the victim's vital signs, specifically those of pulse rate, blood oxygen saturation ($SpO_2$) level, and temperature. The rod detector 2 further comprises a processor (CPU) and indication means united in a single component in the form of a microcomputer 10 with a display screen 11, such as a Motorola, Nokia or Samsung cellular phone or a Sony™ Clie™, IPAQ™ or Palm™ PDA family, which is mounted on the detector 2 near the handle 6 so as to face its operator during use. The detector 2 is electrically connected via wires (not shown) situated within the interior of the shaft 4 of the detector 2 to the detector head 7.

The shaft 4 of the rod detector 2 according to the present invention has a diameter of about 5 cm. The rod detector 2 is preferably telescoping to enable the operator to vary its length as desired, with the varying length of the detector 2 ranging approximately between 75 cm and 300 cm. The slender and telescoping design of the rod detector 2 allows the operator to reach and diagnose victims who are located at a remote, inaccessible location from the operator. One such situation includes contaminated or infected victims that the operator desires to diagnose but from which he/she must keep a safe distance. Another example includes victims who are trapped and buried, and which may only be accessible by a small hole or crevice through which the slender rod detector 2 may be inserted.

Figure 3:
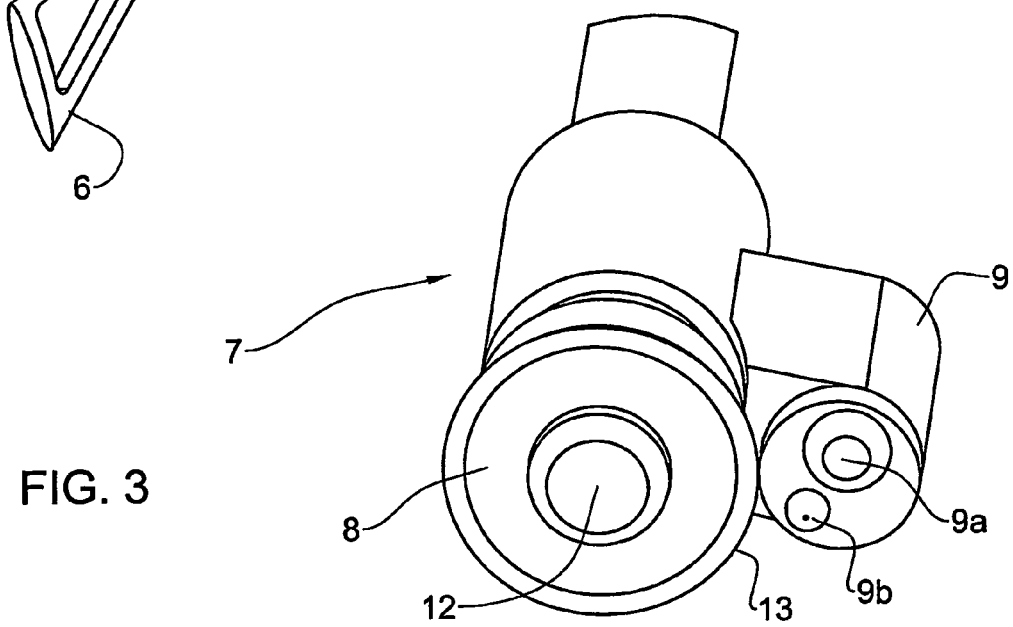
FIG. 3 shows an enlarged detailed view of the sensor of the detector shown in FIGS. 1 and 2.

One example of the optical sensor 8 of the detector head 7 is shown in an enlarged view in FIG. 3, and is a known and commercially available reflectance $SpO_2$ pulse oximeter, such as those manufactured by the companies of Nonin, SPO Medical, Nellcor, and Masimo. The sensor 8 comprises optical system 12 designed to contact or nearly contact a victim's body and a light source (not seen) capable of emitting red and infrared light. The optical system 12 and light source cooperate with the sensor's internal reflectance mechanism (not seen), which receives reflections of the emitted light though the optical system 12. Such reflections, when returning from the body of a victim, are indicative of the victim's vital signs, and the sensor 8 is adapted, upon receipt of these reflections, to generate and to transfer to the microcomputer CPU with screen and input-output ability 10 signals corresponding thereto.

The detector head 7 also includes an opaque protective cover 13 surrounding the sensor 8 and designed to protect it from damage, as well as to contact the victim's body during sensing of his/her vital signs and to thereby shield the sensor 8 from external light which may affect its sensing accuracy. The sensor 8 and cover 13 are joined to the head 7 by a spring-biased attachment (not shown) to enable regulation of the pressure by which the head 7 contacts a victim's body by preventing the sensor 8 and cover 13 from being pressed so strongly against a region of the victim's body as to affect the blood flow in the region and therefore the accuracy of the sensing. The spring-biased attachment may be connected to the computer 10 to also serve as a means for indicating whether contact or sufficient proximity of the sensor to the victim's body has been achieved to enable sensing.

The detector head 7 further includes a visual system 9 mounted thereon and adapted to aid the operator of the rod detector 2 to locate victims. The system 9 includes cameras 9a capable of capturing both video and infrared images to be transferred to and displayed by the computer 10. The infrared images are processed by the computer 10 so as to determine and indicate areas in which victims may be located. The visual system 9 also includes a projector 9b for illuminating the detector's foreground and providing a sufficiently bright environment for the camera to capture video color images.

The computer 10 is adapted to receive signals from the sensor 8 that are indicative of the victim's pulse rate, $SpO_2$ level, and temperature, and to process them in order to provide a qualitative diagnosis as to whether the victim is alive. This diagnosis is displayed on the screen 11 of the computer 10, as explained below. The computer 10 also comprises control button 10a for activating and otherwise operating the rod detector 2.

The computer 10 of the rod detector 2 according to the present invention includes a computer program with an algorithm designed to determine whether a victim suits a health condition of "alive", which is defined by a range for each of the vital signs of pulse, $SpO_2$ level, and temperature. The range for each of these vital signs is characteristic of the state of being "alive" i.e. spans values expected of a living person. The computer 10 is adapted to receive signals from the sensor 8 indicative of the three vital signs and to translate these into measured values. The algorithm is further designed to produce a qualitative diagnosis that the victim sensed is alive if any one of the measured values falls within the range defined for its vital sign. The algorithm is also designed to ignore a measured value of a specific vital sign falling outside the range defined for the specific vital sign so that, in essence, the algorithm searches for values that would justify a diagnosis of "alive". Hence, if no measured value falls within the predefined range for its respective vital sign, the algorithm outputs a conclusion that the health condition of "alive" is not detected.

Preferably, the algorithm is defined to include, for each vital sign, a full possible scope of values that may be measured by the detector. This scope includes the range of values defined as being characteristic of a victim who is alive, with the remainder of the scope defining error values.

The "alive" range is divided into several sub-ranges, which span the entire range but do not overlap. Each sub-range spans values indicative of a different state of a victim's being "alive", such as "normal" and "high rise", and each of these states is pre-assigned a different level of priority by which it is selected in the algorithm. The algorithm is designed to receive a value for each sensed vital sign from the processor and to determine the sub-range in which it falls. The algorithm subsequently determines the state spanned by the determined sub-range for each vital sign and selects the state having the highest level of priority, on which it further bases its qualitative diagnosis. This diagnosis may subsequently be displayed on the screen 11 of the detector's computer 10 in different ways.

FIGS. 4A–7 show a possible manner in which the algorithm of the detector 2 according to the present invention may operate, as well as possible ways in which the resulting diagnosis may be qualitatively indicated to its operator. FIG. 4A shows a flowchart of the algorithm, which begins with the input 20 of pulse, $SpO_2$, and temperature values from the computer's processor. These values are obtained by the sensing of a victim's vital signs by the sensor and the transfer of signals indicative thereof to the computer 10 for processing. The value of each vital sign is analyzed to determine 22 the victim's state of health as predefined by a set of sub-ranges, each spanning values characterizing a different state as shown by tables T1, T2, and T3 for $SpO_2$, pulse, and temperature respectively.

Together, the sub-ranges of each vital sign span all of the values that could possibly result from the sensing of the victim, so that every value necessarily falls within one of the sub-ranges. Furthermore, the sub-ranges do not overlap, thereby ensuring that every value belongs to only one of the sub-ranges and is therefore indicative of only one state.

According to the present invention, for the determination of the Vitality Index from a given physiological or other medical parameter value, a multi-linear search is performed in the proper row in the Vitality Index Working Table:

TABLE T1

Vital Sign: $SpO_2$ %:

| Range | State | Priority |
|---|---|---|
| <64 | Error Level | 5 |
| 65–79 | High Risk Level | 4 |
| 80–91 | Risk Level | 3 |
| 92–94 | Deviant Level | 2 |
| 95–100 | Normal Level | 1 |
| >100 | Error Level | 5 |

Table T1, for example, shows five sub-ranges of values for the sensed $SpO_2$ level of a victim. Each sub-range characterizes a different state for the victim and each is assigned a different priority level as shown in Table T1. The five states, in order of decreasing priority, are: "normal", "deviant", "risk", "high risk", and "error." The first four states (i.e. all excluding that of "error") are indicative of the victim's being alive, while the "error" state indicates that the value of the sensed vital sign falls outside of the range of values expected of a living victim. In such a case, it is possible that the victim is dead, but this can only be established for sure by a trained health professional.

Figure 4B:
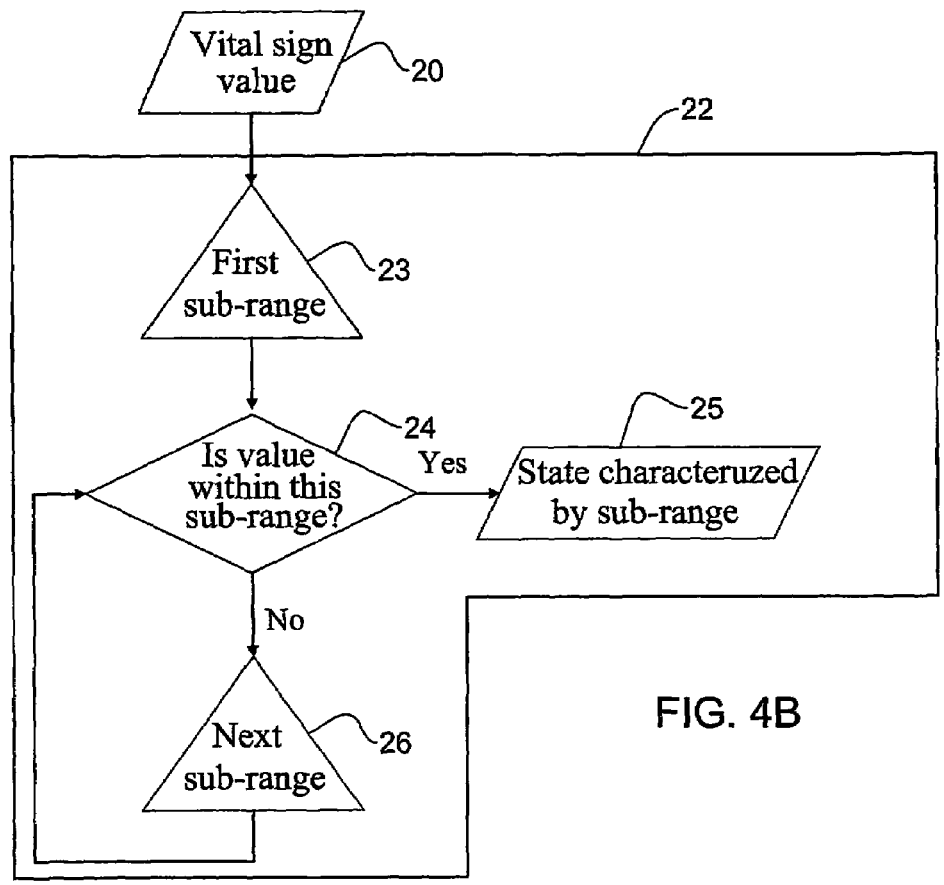

The step in FIG. 4A of determining 20 the state is shown with greater detail in FIG. 4B. Using the data included in Table T1, for example, the state of health of a victim based on the victim's $SpO_2$ level is determined 22 in accordance with the flow chart shown in FIG. 4B. The value of the $SpO_2$ level is received 20 as input into the algorithm, which proceeds to compare this value to the first sub-range 23 i.e. the sub-range having the highest priority, which in this case is indicative of the state of "normal", and to evaluate 24 whether this value falls within the first sub-range. If the value falls within the first sub-range, the algorithm outputs 25 the state indicative of the sub-range based on the vital sign of $SpO_2$ level. However, if the value does not fall within the predefined first sub-range, the algorithm proceeds to compare it with the next sub-range 26 i.e. the sub-range having the next highest priority level, and returns to the previous step to evaluate 24 whether this value falls within this sub-range. This comparison and evaluation of the value continues until the state characterized by the value is determined.

TABLE T2

Vital Sign: Pulse

| Range | State | Priority |
|---|---|---|
| <29 | Error Level | 5 |
| 30–44 | High Risk Level | 4 |
| 45–49 | Risk Level | 3 |
| 50–59 | Deviant Level | 2 |
| 60–100 | Normal Level | 1 |
| 101–120 | Deviant Level | 2 |
| 121–180 | Risk Level | 3 |
| 181–250 | High Risk Level | 4 |
| >250 | Error Level | 5 |

TABLE T3

Vital Sign: Temperature in ° C.:

| Range | State | Priority |
|---|---|---|
| <25 | Error Level | 5 |
| 25.0–32.5 | High Risk Level | 4 |
| 32.5–34.9 | Risk Level | 3 |
| 35.0–35.9 | Deviant Level | 2 |
| 36.0–36.9 | Normal Level | 1 |
| 37.0–37.9 | Deviant Level | 2 |
| 38.0–38.9 | Risk Level | 3 |
| 39.0–43.9 | High Risk Level | 4 |
| >44 | Error Level | 5 |

The above-described determination of the state is simultaneously performed in the same manner, i.e. as shown in FIG. 4B, for the value of each of the sensed vital signs, which in the present example include pulse and temperature, whose data appear in tables T2 and T3, respectively, arranged similarly to the $SpO_2$ table T1.

Reverting to FIG. 4A, after the states have been determined 22 for the three vital signs based on each of their input values, the algorithm proceeds to select 27 the state having the highest priority from among those determined. Thus, for example, if at least one of the vital signs is evaluated as having the state of "normal", this will be the selected state since it has the highest possible priority level. The output of the selected state 28 is indicative of whether the victim is alive and, in the affirmative, his/her deviation from an optimal state of living.

The algorithm subsequently proceeds to determine the manner in which a qualitative diagnosis based on the selected state will be presented to the operator. This depends on whether the detector is in "Life Detector Mode" and is being used to perform a "one-time" detection of whether the victim is alive, or whether the detector is in "Life Monitor Mode" in which it is directed to "continuous detection" or monitoring of the victim. The computer 10 preferably includes means for enabling the operator to toggle back and forth between these modes, but the detector 2 must always be in only one of these modes in order to operate. The algorithm continues by evaluating 29 whether the detector is in "Life Monitor Mode", and if it is not, it is assumed to be in "Life Detector Mode".

Figure 5A:
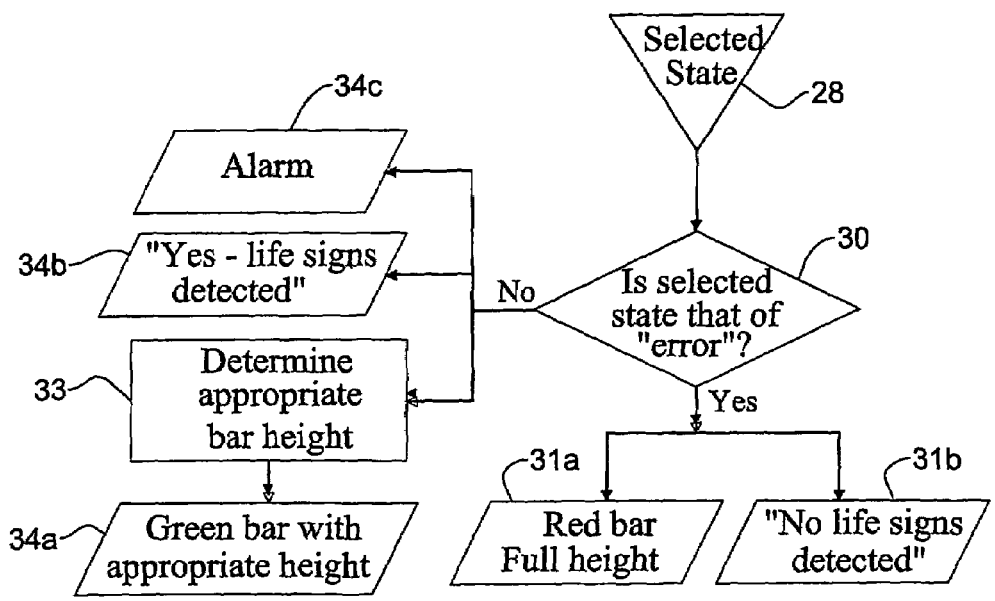
FIGS. 5A–5D show flowcharts and indications for qualitative diagnoses in another embodiment of the detector in accordance with the present invention.

FIG. 5A shows the continued steps of the algorithm when the detector 2 is in "Life Detector Mode". The selected state 28 is evaluated 30 by the computer 10 to determine whether it is the state of "error". If so, the algorithm produces the instruction output 31a for the computer 10 to display to the operator on the screen 11 a qualitative diagnosis of the victim's condition in the form of a rectangle 32 whose area is filled with a red bar, along with an instruction output 31b to display the words "No life signs detected" as shown in FIG. 5B.

Figure 5B:
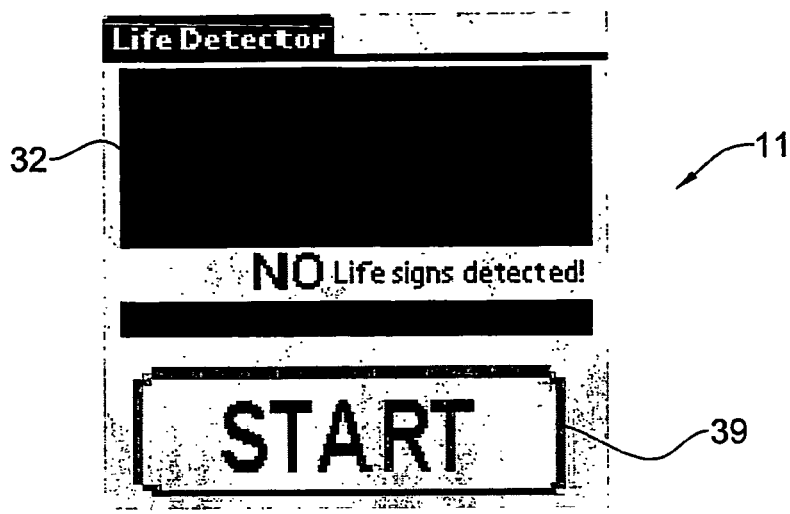
Figure 5C:
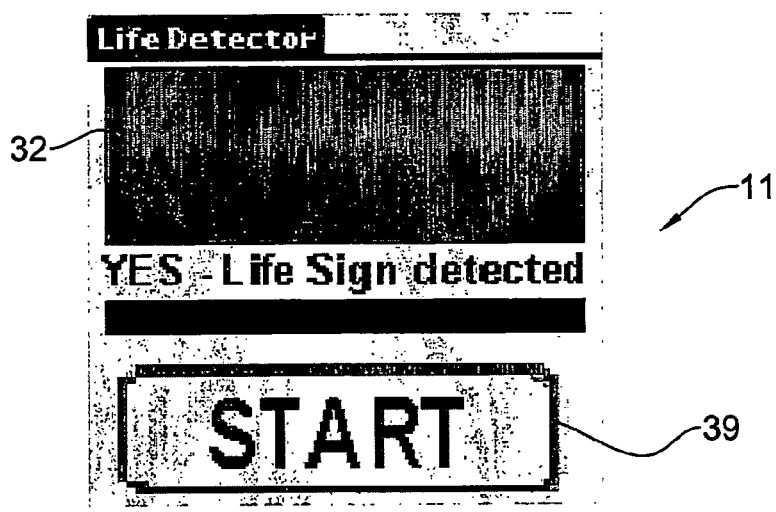

Reverting to FIG. 5A, if it is evaluated 30 that the selected state is not that of "error", the victim is alive and the algorithm first determines 33, based on the selected state, how high the rectangle 32 will be filled with a green bar in accordance with the table shown in FIG. 5C to correspondingly indicate the extent to which the person is alive i.e. of optimal state of health. For example, if the selected state is "deviant", the rectangle 32 will be filled to 75% of its total height. The algorithm proceeds to produce an instruction output 34a for the computer 10 to display to the operator on the screen 11 a qualitative diagnosis of the victim's condition in the form of a rectangle 32 whose area is filled to the determined height with a green bar. Two additional instruction outputs 34b and 34c are produced to simultaneously display along with the green bar the words "Yes—life signs detected", and to sound an audible alarm, all in order to qualitatively indicate to the operator that the victim is alive. FIG. 5C shows an example of the computer screen 11 displaying such results for a victim found to be in a "normal" state of health, as indicated by the rectangle 32 being filled to 100% of its height with a green bar.

Figure 5D:
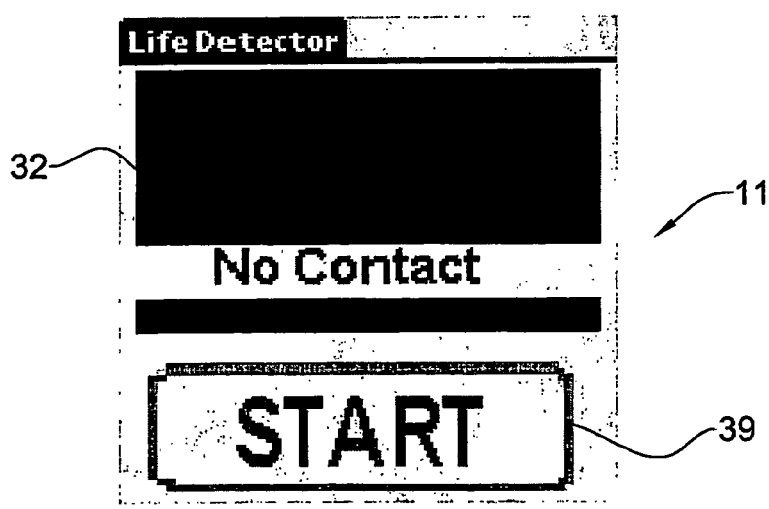

As shown in FIG. 5D, if the sensor of the detector 2 in accordance with the present invention fails to make sufficient contact with the victim, the detector 2 may have means connected to the computer 10, such as the aforementioned spring-biased attachment, for indicating to the operator that "No Contact" with the victim has been established. In such a case, another attempt at sensing, if possible, should be made.

FIGS. 5B, 5C, and 5D show the screen 11 as a touch screen displaying a large "START" button 39, which may be touched by the operator in order to recommence the sensing and diagnosis, e.g. to re-examine a previously diagnosed victim to validate results, to monitor any change in the victim's condition, to examine a different victim, or to make another attempt at sensing after receiving a "No Contact" indication. The screen can display simple instructions on how to work the system with Help, Start and Stop key functions that may be activated by touch, voice or other capability.

There may be a few modes of work, one for medical operator with professional training and another, standard mode for operator with no medical background. The screen may alarm if there is no sensor connection or bad signal or any other input error. The screen has the ability to alarm in color coded mode. The main task of detecting life signs may appear in colored more declaring there are vital signs in normal, deviated, risk or high risk level. There is an option to save the data input notes, change the limits and alarm thresholds. There is an option to transmit the data as well.

Note: When there are no life signs detected, this still does not mean the victim is lifeless but rather means that the system did not find such signs. Accordingly, the system would never pronounce "dead" but will readily declare "alive" when a life sign is found and may as well indicate the level of normalized values.

Figure 6A:
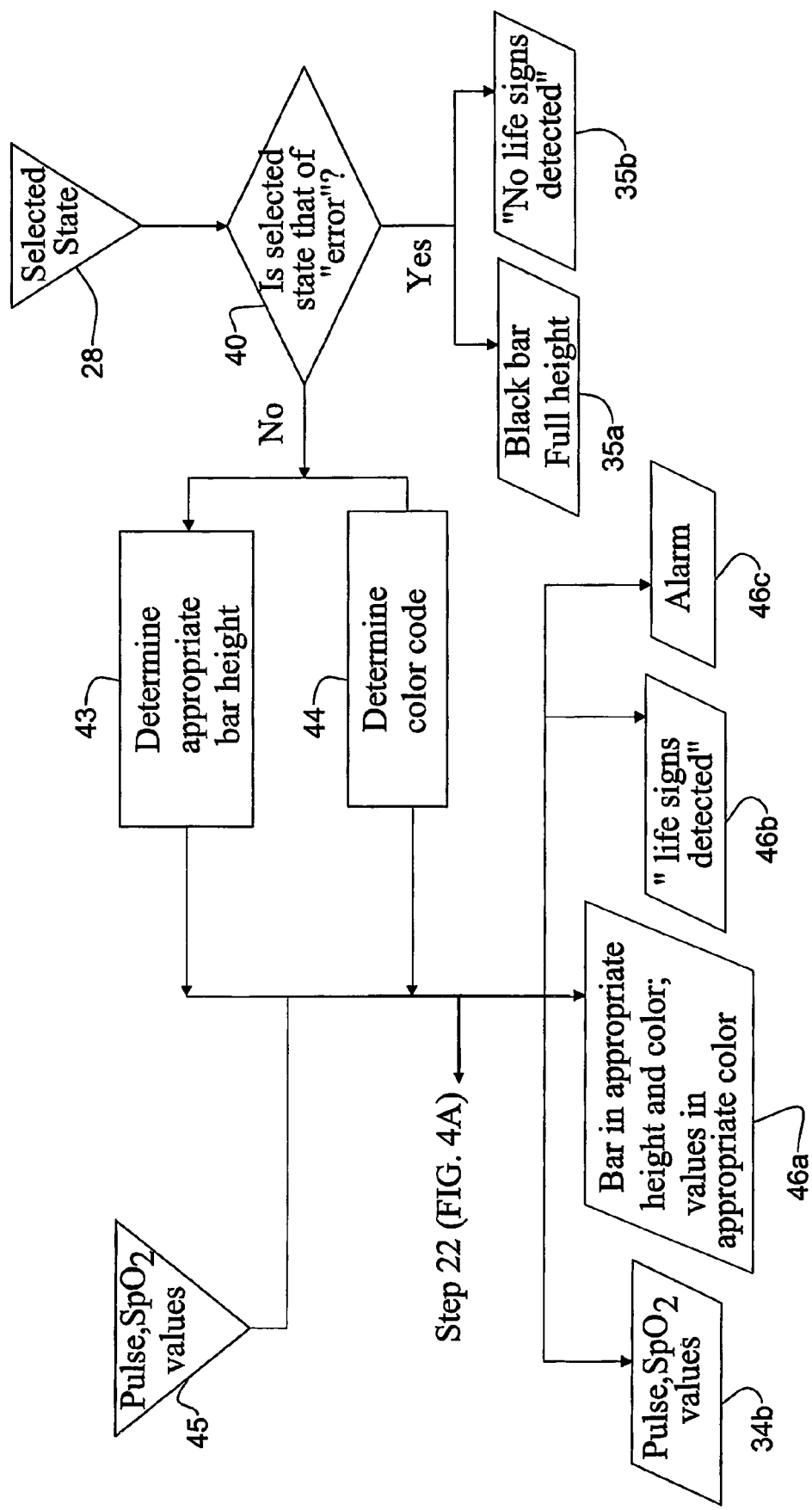
FIG. 6A is a continuation of the algorithm shown in FIG. 4A.

FIG. 6A shows the continued steps of the algorithm from FIG. 4A when the detector 2 is in "Life Monitor Mode". The selected state 28 is evaluated 40 by the computer 10 to determine whether it is the state of "error". If so, the algorithm produces the instruction output 35a for the computer 10 to display to the operator on the screen 11 a qualitative diagnosis of the victim's condition in the form of a rectangle 36 whose area is filled with a black bar, along with an instruction output 35b to display the words "No life signs detected" as shown in FIG. 5B.

TABLE T4

| State | Fraction of Total Height |
| --- | --- |
| Normal | 100% |
| Deviant | 75% |
| Risk | 50% |
| High Risk | 25% |

TABLE T5

| State | Color |
| --- | --- |
| Normal | Green |
| Deviant | Yellow |
| Risk | Orange |
| High Risk | Red |

Figure 6B:
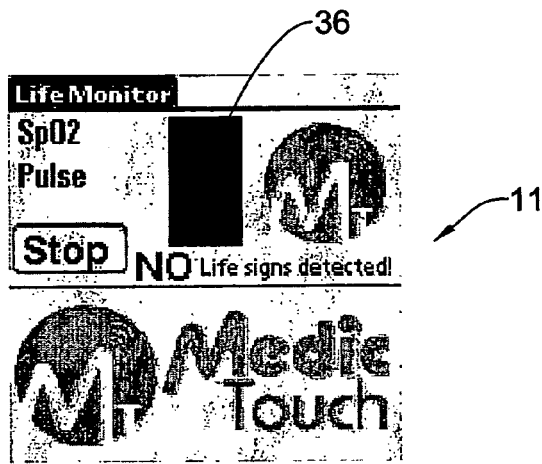
FIGS. 6B–6E show various diagnostic results on the indicator of the detector.

Reverting to FIG. 6A, if it is evaluated 40 that the selected state is not that of "error", the victim is alive and the algorithm determines 43, based on the selected state, how high the rectangle 36 will be filled with a bar in accordance with Table T4 as explained above to correspondingly indicate the extent to which the person is alive i.e. of optimal state of health. The algorithm simultaneously determines 44 the color of this bar based on the selected state in accordance with Table 6B. The algorithm also obtains the numerical values 45 of the victim's sensed pulse and SpO$_2$ level and proceeds to produce an instruction output 46a for the computer 10 to display to the operator on the screen 11 a qualitative diagnosis of the victim's condition in the form of a rectangle 36 whose area is filled to the determined height with a bar having the determined color (FIG. 6B). The additional instruction outputs 46b and 46c are produced to simultaneously display along with the colored bar the words "Life signs detected", and to sound an audible alarm, all in order to qualitatively indicate to the operator that the victim is alive. Furthermore, an instruction output 46d is produced to instruct the computer 10 to further display on the screen 11 the numerical values of the victim's pulse and SpO$_2$ level color-coded with the same color as the bar. Since it is in the "Life Monitor mode" and is directed to continuously assess the condition of the victim, as the detector 2 produces the outputs 46a–46d and displays its qualitative diagnosis, the computer 10 instructs the sensor to resume sensing the victim and the algorithm returns to the step of receiving the sensed vital sign values 22 as shown in FIG. 4A.

Figure 6C:
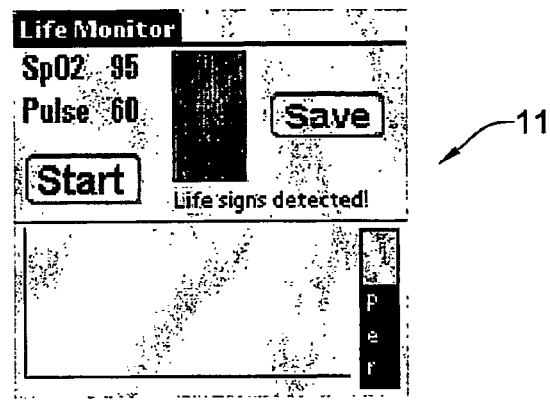
Figure 6D:
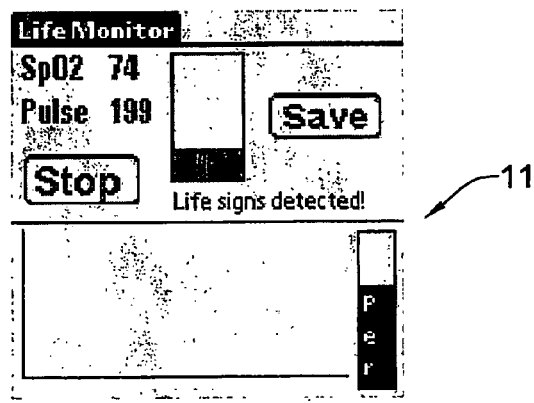
Figure 6E:
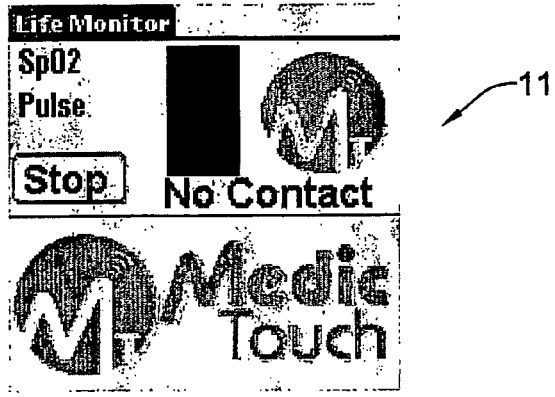

FIG. 6C shows an example display of the computer screen 11 displaying such results for a victim found to be in a "normal" state of health, as indicated by the rectangle 36 being filled to 100% of its height with a green bar. FIG. 6D shows another example display of the screen 11 with results for a victim found to be in the "high-risk" state, as indicated by the rectangle 36 being filled to 25% of its height with a red bar. FIG. 6E shows the screen 11 displaying the words "No Contact", as would occur when the detector 2 in accordance with the present invention fails to make sufficient contact with the victim to sense his/her vital signs.

FIG. 9 shows another embodiment of the detector of the present invention in the form of a hand-held detector unit 82. The unit 82 is similar to the detector 2 shown in FIGS. 1 and 2, but differs in that it lacks the shaft 4 and the handle 6 as it is designed to be more fully held by the operator and to be used in cases where the operator has greater access to the victim. The unit 82 is particularly advantageous for disaster and accident situations in which the victims are directly accessible, such as when spread over open ground. The unit 82 is small and lightweight allowing for it to be easily transported and therefore minimizing the time needed to move between victims. The unit 82 may include means by which it may be held and carried in the form of a glove (not shown). Such a glove provides an ergonomic means for the operator to transport the unit, as well as affording the operator with protection from the sensed victim and his/her immediate surroundings.

FIG. 10 shows yet another embodiment of the detector of the present invention in the form of a cable detector 92. The cable detector 92 is similar to the rod detector 2 shown in FIGS. 1 and 2, but differs in that it lacks the handle 6 and that the shaft 4 is replaced by a long, high strength cable 94. The cable detector 92 is designed for use in situations where the victims are not directly accessible to the operator and are located at a considerable distance therefrom, such as in the case of victims trapped in a collapsed mine. The detector cable 92 may be lowered, for example, into the mine to locate victims, as well as to sense and diagnose them by dropping the detector head 7 onto their bodies.

Figure 11:
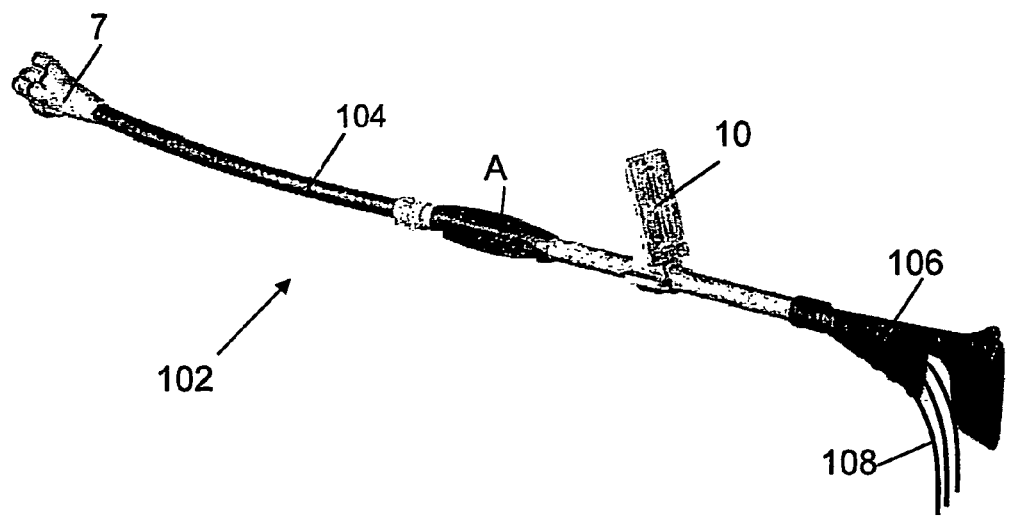
FIG. 11 shows an embodiment of the life detector with flexible telescope rod.

FIG. 11 shows one more embodiment of the detector of the present invention. The flexible detector 102 is similar to the rod detector 2 shown in FIGS. 1 and 2, but differs in that it has a flexible shaft 104. The handle 106 is shown with a port 108 for power cables, flexible tubes and other lines which may be used with the detector.

Figure 12:
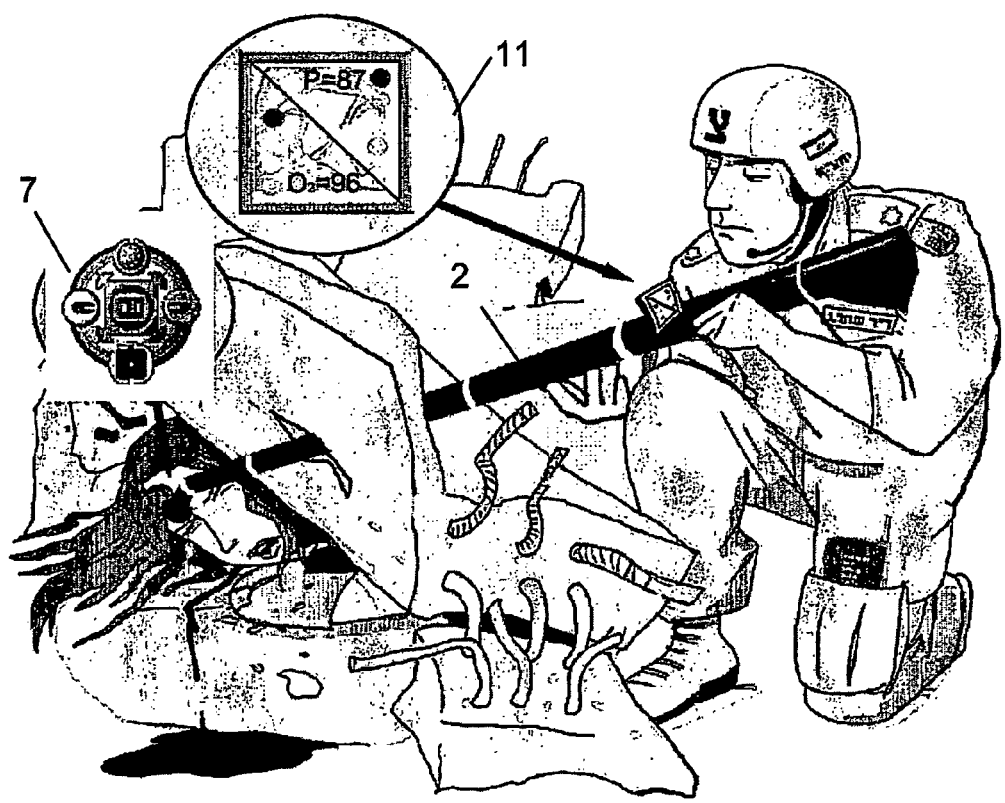
FIG. 12 shows the application of the life detector in a disaster area.

In operation, the rod detector 2 shown in FIGS. 1, 2 or 11 is carried by an operator at the site of recent disaster. The operator carries the rod detector 2 by the handle 6 and holds it out in front of him. The detector 2 is first used to locate a victim of the disaster. The visual system 9 aids the operator in locating a victim by displaying video color and thermal images, which may be superposed, on the screen 11 of the computer 10. It may be necessary to insert the detector head end of the shaft 4 of the rod detector 2 into various holes, bores, and crevices that may be found the debris of the disaster site in order to locate victims that may be trapped or buried underneath the debris (FIG. 12).

Figure 8A:
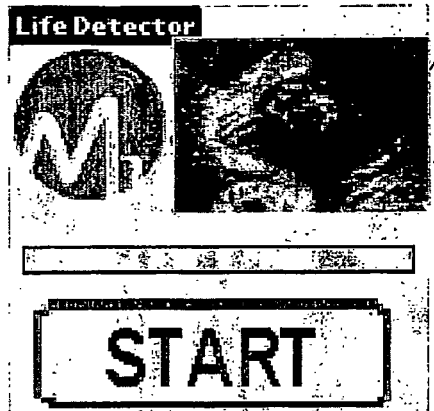
Figure 8B:
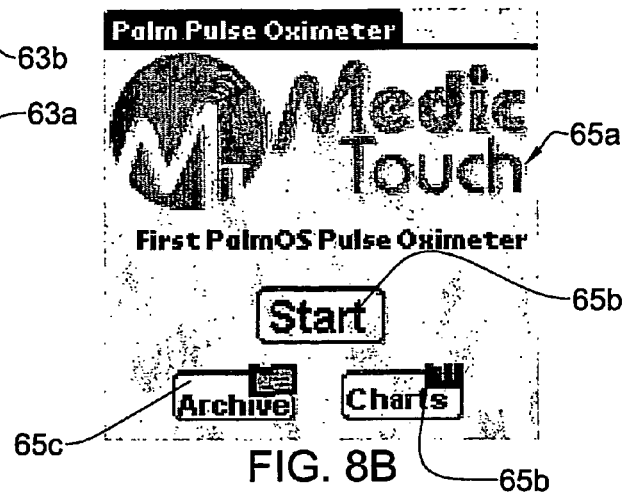
Figure 8C:
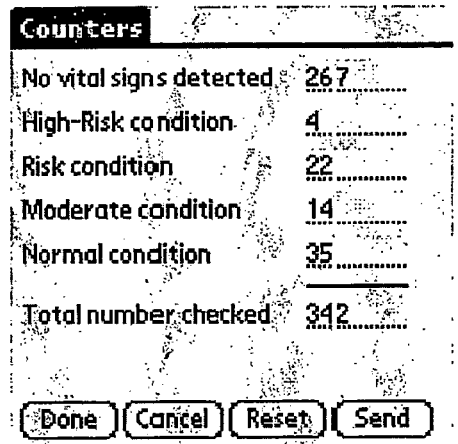
Figure 8D:
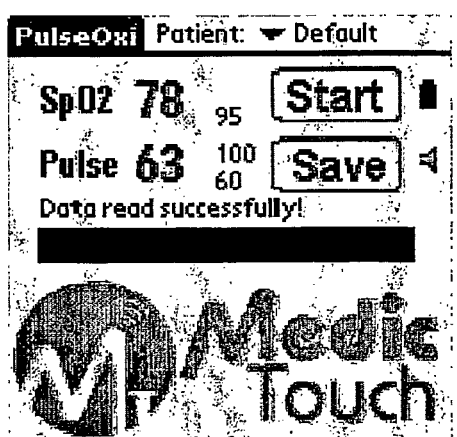
Figure 8E:
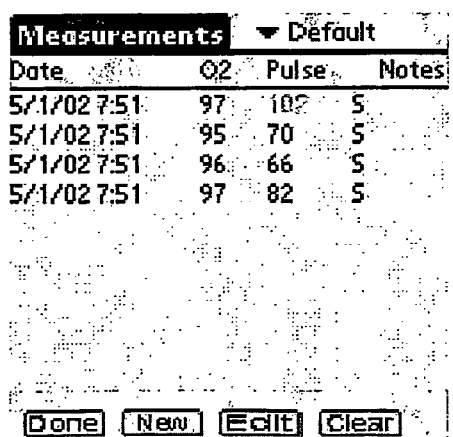
Figure 8F:
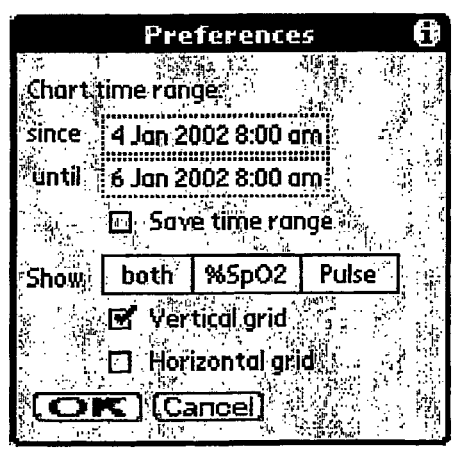

Once a victim has been found, the detector head 7 is pressed up against any exposed and accessible part of the victim's body. As outlined in the flow chart of FIG. 7, the diagnosis process begins by touching the "start" 60 button on the touch screen 11. FIG. 8A shows the "start" screen 63a of the computer 10, when the detector 2 is in "Life Detector Mode". In this mode, the detector 2 begins by displaying a video or infrared image 63b of the victim to be sensed. The "start" screen 65a of the computer when in the "Life Monitor Mode" is shown in FIG. 8B and includes a touch screen "start" button 65b, as well as "archive" and "charts" buttons 65c and 65d, which enable the more advanced features of the computer 10.

Reverting to FIG. 7, after touching the "start" button on screen 63a or screen 65a, the sensor 8 is activated and it begins to sense 62 the victim's pulse, $SpO_2$, and temperature. The computer 10 quickly processes 64 the signals produced by the sensor 8 and indicative of the magnitude of the sensed vital signs, translating them into measured values. These values are provided as input into the computer's algorithm, which proceeds to analyze 66 them as described above and shown in FIGS. 4A–6E, depending on whether the detector 2 is in "Life Detector Mode" or "Life Monitor Mode".

For example, the measured values for a given victim may be a pulse of 37, a $SpO_2$ level of 82 and a temperature of 34.5° C. All those values are not normal and on a regular monitor device may some time be out of scale. It means the mechanical or electrical standard device will display error or not normal values. But in this invention this sample will still declare a green life sign because the border line is alive or not. Also, even if in another sample the temperature could not be displayed and $SpO_2$ percentage could not be recognized, while the pulse would be 140, the system will display green and life detecting. It means at least one logic parameter will be sufficient On the other hand, if as well the reported pulse is 0, the detector will display red color and 'No life detected'.

Some advanced features are shown in FIGS. 8C–8I. After gathering the data, the operator may save the data to see the improvement or decline of the total life index with time on a graph or list for every subject that the data have been saved in his database. The "Save" function provides the CPU the ability to scan the saved parameters that are in the memory and draw a colored table 8E or graph 8H for each parameter according to the "life thresholds level" by time or record. The advance mode gives the ability to display by condition level in a table the total number of victims or other recorded data that has been saved. This option gives a statistics of the total number of victims or other distribution by a different sub type of life data. There is an option to have personalized/customized alert limits for each parameter overriding the default level limits (FIG. 8I).

Reverting to FIG. 7, the diagnosis provided 68 as output by the algorithm is qualitatively indicated to the operator by displaying 71 results of the detection that are indicative of whether the victim is alive and to what extent the victim is in good health. The detector 2 also sounds an alarm 72 if the victim is determined to be living so as to quickly and qualitatively alert the operator to the condition in a manner which may easily be understood by a non-health professional. The detector 2 may also transmit 73 the diagnosis to a remote location, such as by sync to a remote server, locally to Infrared, Blue Tooth™, or similar technologies, transmission to a cellular phone, as well as long distance transmission as by radio transmission (RF). In this way, the diagnosis of one or a plurality of victims may be reviewed, as well as further analyzed by the operator as well as by additional persons located off-site.

Subsequently, the detection process automatically stops 75, unless the detector 2 is in "Life Monitor Mode" 76, in which case the sensor 8 is reactivated to sense 62 the vital signs of the victim and the process repeats indefinitely to thereby monitor the victim's condition. Regardless of the mode the detector is in, the process may always be arrested by pressing the "stop" button on the screen 11.

Depending on the diagnosis, the victim may be immediately treated or tagged with an indication of the diagnosis so as to be identifiable as a victim who does or does not require immediate medical attention and/or evacuation.

Figure 13:
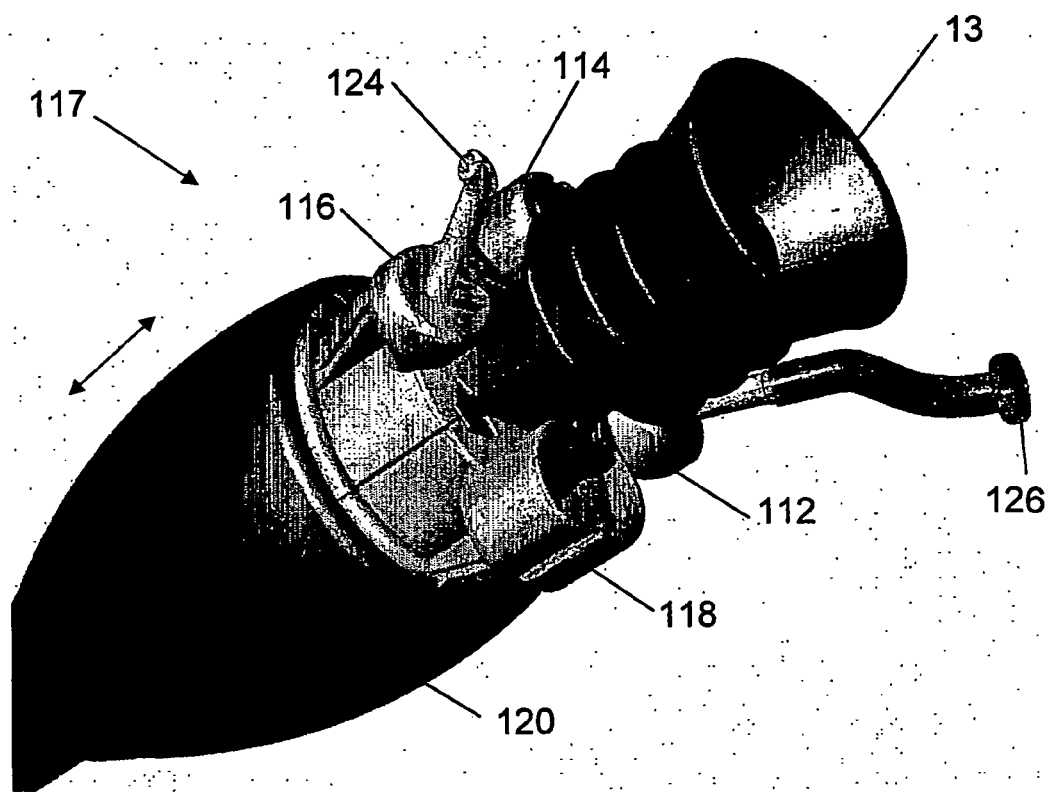
FIG. 13 is a perspective view of a detector head with modular design.
Figure 14:
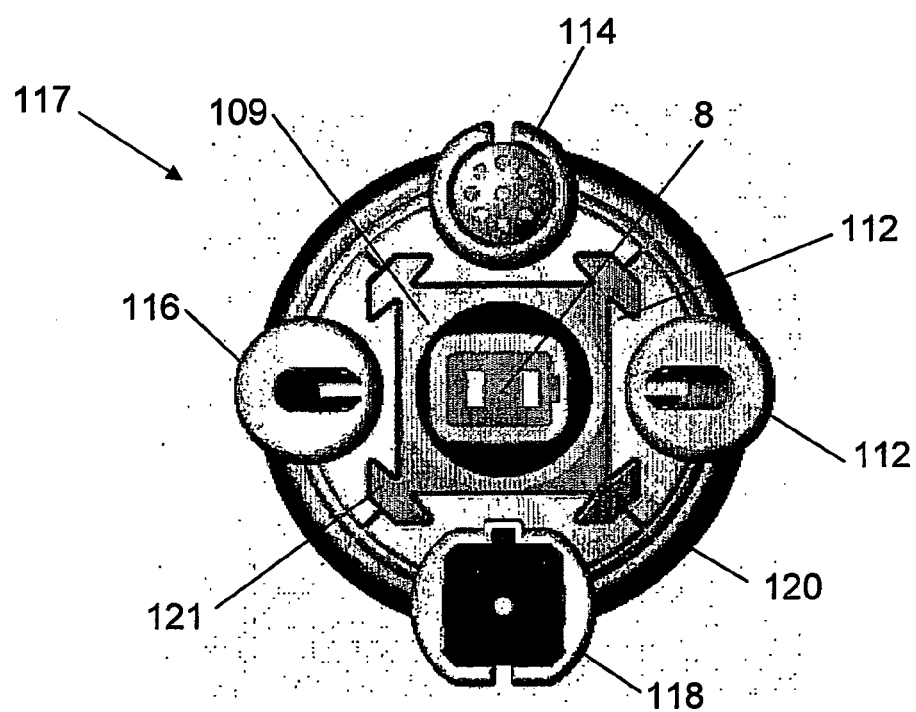
FIG. 14 is a front view of the detector head of FIG. 13.
Figure 15:
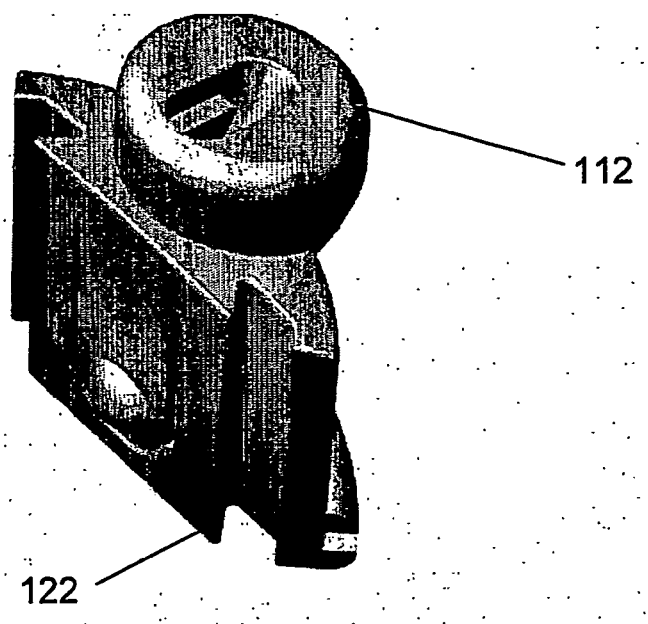
FIG. 15 shows a changeable module for the detector head of FIG. 13.

With reference to FIGS. 13 and 14, there is shown a detector head 107 which differs from the head 7 in its modular design. The modular head 107 comprises a central permanent core 109 fixed to the end of the shaft (not shown) and a number of changeable modules 112, 114, 116 and 118 secured in place by a slidable ring 120. The core 109 accommodates the optic sensor 8 and its protective cover 13 (removed in FIG. 14). The core 109 has locking elements on its periphery, for example dove-tails 121, for assembly with mating elements 122 of the changeable modules (see also FIG. 15).

Figure 16:
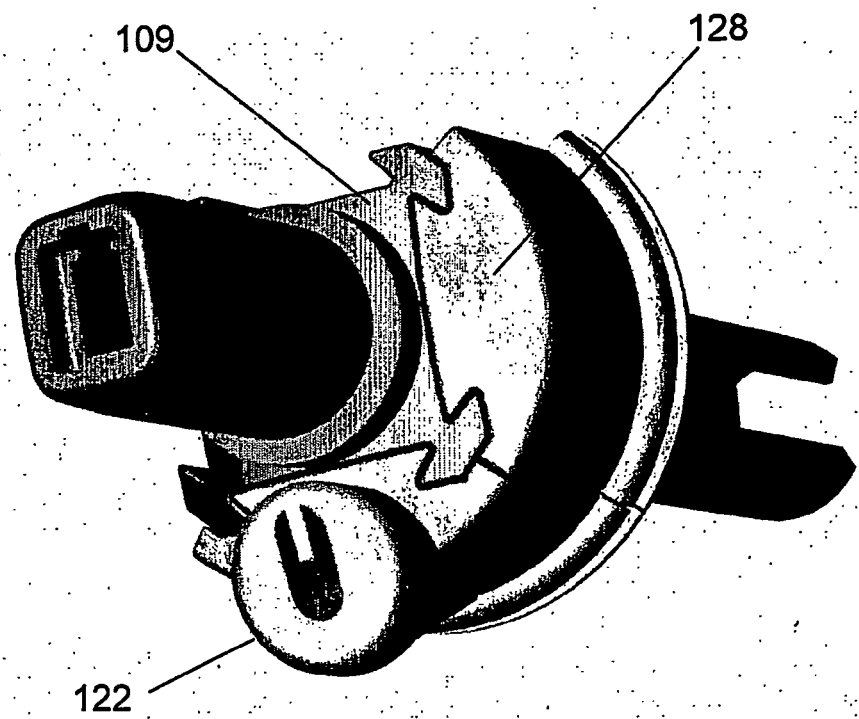
FIG. 16 illustrates the assembly of the detector head of FIG. 13 with a dummy module.

Changeable modules may be designed to perform various functions as needed for the current task of the detector and operator. As an example, FIGS. 13 and 14 show two pipe holders 112 and 116—one for oxygen (nozzle 124) and one for water (nozzle 126), a compound speaker-microphone 114, and a camera 118. The necessary wires and tubes are obtained through the tubular shaft and terminate in suitable standardized connectors at the matching surfaces of the core 109. If not all functional modules are necessary, each of them can be substituted by a dummy module 128, as shown in FIG. 16.

Figure 17:
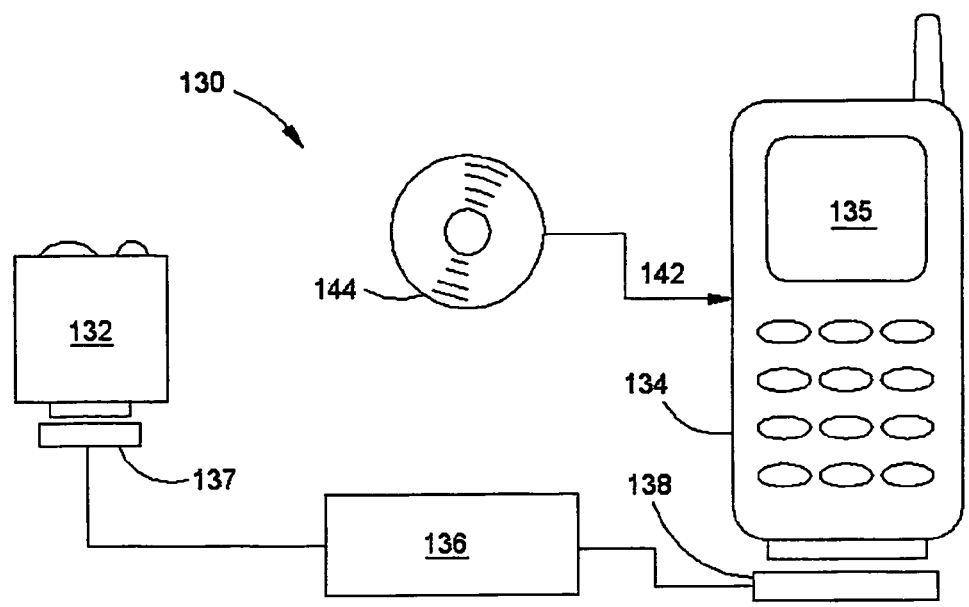
FIG. 17 is a schematic view of a detector of the present invention assembled by means of a cable adapter.

With reference to FIG. 17, there is shown the principle scheme of an embodiment 130 of the life detector of the present invention comprising a standard medical sensor 132, a standard programmable communication device (PCD) 134 with indicator 135, and a medical cable adapter 136. The medical sensor 132 may be the above-described optical pulse oxymeter 8, for example Nonin. The communication device 134 may be a programmable cellular phone like Sony or Motorola, or a PDA with wireless connection.

Figure 18:
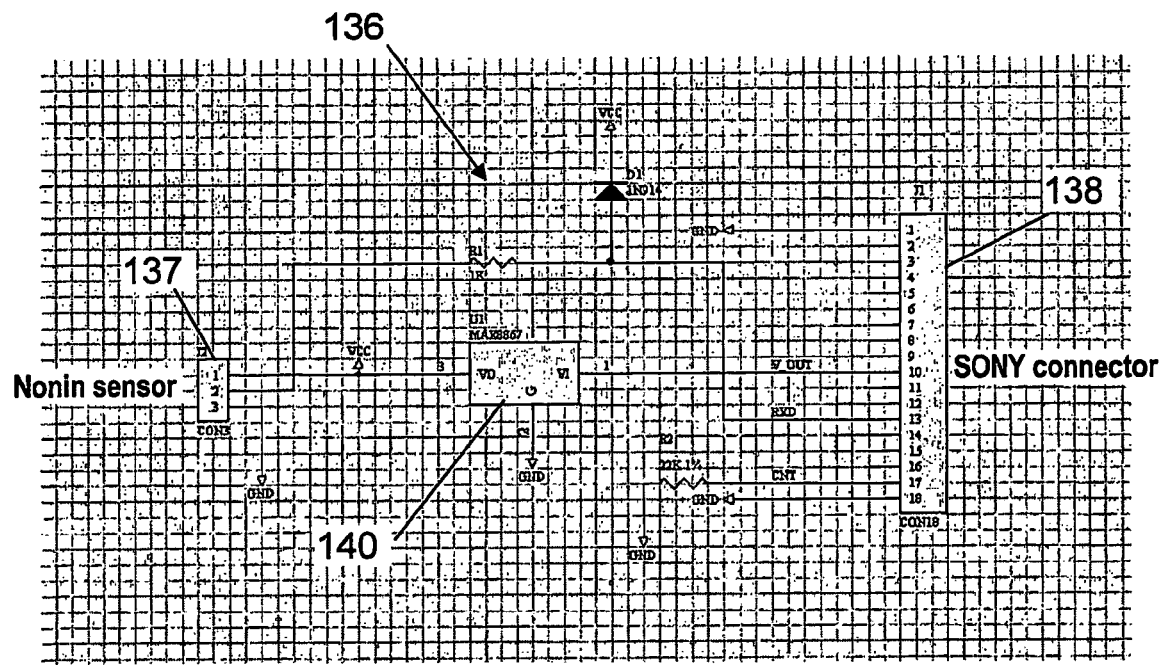
FIG. 18 is an exemplary circuit of the cable adapter in FIG. 17.

With reference also to FIG. 18, the cable adapter 136 includes a first standard connector 137 to the sensor 132, a second standard connector 138 to the device 134, and a microprocessor circuit board 140 without power source. The cable adapter 136 is designed, specifically for each kind of sensor 132 and communication device 134, to maintain correct input and output voltages, to scale the signal data amplitude and frequency both ways, and to provide electric power from the communication device to the sensor. A service (driver) program 142 and other data are prepared specifically for the PCD 134 and for the sensor 132. The driver program is kept on standard media 144 such as disk, flash card, or resides in another computer or in an internet website. The driver program is downloaded into the PCD memory in the standard way provided for the PCD 134. The cable adapter 136 shown in FIG. 18 is designed specifically for use with a Nonin Sensor and a Sony cellular phone, however it may be designed to interface a number of different devices 134 to a number of different sensors 132, in dependence on their connectivity and programmability.

In operation, when the connectors 137 and 138 are plugged, the cable adapter 136 transforms the programmable communication device 134 into a control, indication and communication panel of the life detector 130, which will also have the ability to transfer data to a remote location. Understandably, if data transfer is not needed, other, non-communication devices may be used instead of the PCD. Such cable adapter may be used for other purposes involving application of a medical sensor together with a general-purpose PCD, especially when the only source of power is in the PCD.

The above described embodiments are only examples of a life detector adapted to determine whether a victim suits a health condition in accordance with the present invention, and that the scope of the present invention fully encompasses other embodiments which may become obvious to those skilled in the art. For example, the detector according to the present invention may be used to detect whether organisms other than humans are alive, including animals and microorganisms. This may be particularly useful in missions to other planets, where new life forms may be found and assessment of their life condition may be desired.

Other embodiments of the life detector may provide a quick qualitative detection of living bacteria from specific volatile vapors or fluorescent light emitted from that bacteria. Bacteria strains of *Escherichia coli, Klebsiella pneumoniae*, microorganisms *Proteus mirabilis, Staphylococcus aureus, Staphylococcus saprophyticus, Enterococcus faecalis*, as well many others have special emission characteristics that can be recorded when the bacteria are alive, and are diminished or modified in other cases. A number of microorganisms discharge characteristic gases that can be detected, like methane and $CO_2$ when they are in life cycle. When analyzing more than one set of unique parameters, a very high level of confidence may be achieved for a quantitative diagnosis that the specific microorganisms are alive. In the same way the fluorescent light emitted from microorganisms, reflected light (color), or pulsatile behavior may help in characterizing their type and diagnose if they are alive or not.

Still other embodiments of the life detector may provide a quick diagnosis of the life or health condition of bodily parts which may be different from the health condition of the whole organism, for example external transplants of limbs, individual teeth, etc. In a disaster or technology accident area, limbs with tourniquets and even severed limbs may be quickly diagnosed for deciding ways and measures of treatment.

The invention claimed is:

1. A life detector adapted to be used to determine whether an organism or part thereof suits a life condition predefined by a set of ranges, each for a physiological parameter and each characterizing said life condition, the detector comprising a sensor unit adapted to sense at least two of said physiological parameters and to generate signals indicative of their values, a processor for receiving and processing said signals to arrive at said values, the processor further being adapted to disregard any value falling outside the range of the respective parameter and to produce a qualitative diagnosis based on values falling within its range, the diagnosis being indicative of whether said organism or part thereof suits said life condition, the detector further comprising indication means adapted to indicate said diagnosis.

2. The life detector according to claim 1, wherein the range of each of said at least two parameters includes a predefined set of sub-ranges, each characterizing a particular state within said life condition and each having a predefined priority level with respect to said life condition, said processor being further adapted to determine the particular sub-range in which the value of each parameter falls and the state characterized by said sub-range, and to produce a qualitative diagnosis based only on the state having the highest priority level.

3. The life detector according to claim 1, wherein said detector is adapted to be used by a human operator.

4. The life detector according to claim 1, wherein said indication means is adapted to indicate said diagnosis to a human operator.

5. The life detector according to claim 1, wherein said organism is a human or an animal and said life condition is health condition.

6. The life detector according to claim 5, wherein said at least two parameters are any two of the following: pulse rate, blood oxygen saturation level, and temperature.

7. The life detector according to claim 6, wherein said detector is adapted to be used by a human operator, said processor and said indication means being adapted to indicate said diagnosis to such human operator who is not a medical professional.

8. The life detector according to claim 5, wherein said sensor unit is adapted to sense said physiological parameters by directly contacting the body of said human or animal.

9. The life detector according to claim 8, wherein said sensor unit comprises an optical sensor.

10. The life detector according to claim 9, wherein said optical sensor is a reflectance pulse $SpO_2$ oximeter.

11. The life detector according to claim 8, wherein said sensor unit comprises an electrocardiograph (ECG).

12. The life detector according to claim 1, wherein said organism is a microorganism, and said life condition is being alive.

13. The life detector according to claim 12, wherein said at least two parameters are any two of the following: fluorescence, reflected light, gas discharge, temperature, and pulsatile behavior.

14. The life detector according to claim 1, wherein said organism is of astrobiology type, and said life condition is being alive.

15. The life detector according to claim 14, wherein said at least two parameters are any two of the following: gas discharge, temperature, and pulsatile behavior.

16. The life detector according to claim 1, comprising a rod with said sensor unit attached thereto.

17. The life detector according to claim 16, wherein said rod is tubular.

18. The life detector according to claim 16, wherein said rod is adapted to change its length.

19. The life detector according to claim 16, wherein said rod is adapted to be operatively and reversibly bent.

20. The life detector according to claim 1, wherein said detector is in the form of a hand-held unit.

21. The life detector according to claim 1, wherein said detector is in the form of a flexible cable with said sensor unit attached to one end of said cable.

22. The life detector according to claim 1, wherein said processor and said indication means are further adapted to indicate said values.

23. The life detector according to claim 1, wherein said indication means comprises at least one of the following: a visual display, an audio indicator, and a vibration indicator.

24. The life detector according to claim 1, further comprising a communication means adapted to transmit at least said diagnosis to a remote location.

25. The life detector according to claim 1, wherein said processor and said indication means are united in a single device.

26. The life detector according to claim 25, wherein said single device comprises a communication means adapted to transmit said diagnosis to a remote location.

27. The life detector according to claim 25, wherein said single device is a programmable cellular phone or a palmtop computer.

28. The life detector according to claim 25, wherein said single device is a general-purpose programmable device (PD), said sensor unit comprises a standard medical sensor, said life detector further comprises a cable adapter interfacing said programmable device to said medical sensor, and a driver program specifically directed to use with said medical sensor, said cable adapter and said PD is loaded in said PD.

29. The life detector according to claim 25, wherein said programmable device has remote communication capability.

30. The life detector according to claim 1, further having means for determining the location of said organism.

31. The life detector according to claim 30, wherein said means for determining the location is at least one of the following: a video camera, a thermal camera, a light source.

32. The life detector according to claim 1, further comprising at least one audio aid of the following: voice microphone, speaker, sound detector, headphones.

33. The life detector according to claim 1, wherein at least said sensor unit is adapted for prolonged association with said organism while said detector is adapted for repeated or continuous production and indication of said diagnosis, thereby providing monitoring of said life condition.

34. The life detector according to claim 33, wherein at least one of said sensor unit and said indication means is detachable from said detector and adapted for remote communication with said detector so that an operator of the detector could perform said monitoring remotely.

35. The life detector according to claim 34, comprising at least one of the following means for treatment: gas supply line, liquid supply line, suction line, power electric line, and mechanical manipulator.

36. The life detector according to claim 1, further adapted to treat said organism.

37. The life detector according to claim 1, wherein said sensor unit comprises a permanent base and at least one changeable sensor module detachably attachable to said base.

38. The life detector according to claim 37, further comprising at least one changeable treatment module detachably attachable to said base.

39. The life detector according to claim 38, wherein said base and said changeable modules have identical means for attachment so that said changeable modules are interchangeable among themselves.

40. The life detector according to claim 39, comprising at least one dummy module which is interchangeable with anyone of said sensor and treatment modules.

41. A method for determining whether an organism or part thereof suits a life condition predefined by a set of ranges, each for a physiological parameter and each characterizing said life condition, including:

sensing at least two of said parameters of the organism and generating signals indicative of their values;

receiving and processing said signals to arrive at said values, including disregarding any value falling outside the range of the respective parameter;

producing a qualitative diagnosis based on any value falling within the range for its parameter, the diagnosis being indicative of whether the organism suits said life condition;

indicating said diagnosis.

42. The method according to claim 41, wherein the range of each of said at least two parameters includes a predefined set of sub-ranges, each characterizing a particular state within said health condition and each having a predefined priority level with respect to said condition, said processing further including:

determining the particular sub-range in which the value of each parameter falls, and the state characterized by said sub-range;

producing said qualitative diagnosis based only on the state having the highest priority level.

* * * * *